(12) United States Patent
Zhou et al.

(10) Patent No.: US 10,253,108 B2
(45) Date of Patent: Apr. 9, 2019

(54) MUTATED ANTIBODY OF FULLY HUMANIZED HER2 ANTIBODY, AND ENCODING GENE AND USE THEREOF

(71) Applicant: Genor Biopharma Co., Ltd., Shanghai (CN)

(72) Inventors: Qing Zhou, Shanghai (CN); Mengjun Shu, Shanghai (CN); Zhuzi He, Shanghai (CN); Jun Lin, Shanghai (CN)

(73) Assignee: Genor Biopharma Co., Ltd., Shanghai (CN)

( * ) Notice: Subject to any disclaimer, the term of this patent is extended or adjusted under 35 U.S.C. 154(b) by 53 days.

(21) Appl. No.: 15/304,199

(22) PCT Filed: Dec. 8, 2015

(86) PCT No.: PCT/CN2015/096674
§ 371 (c)(1),
(2) Date: Oct. 14, 2016

(87) PCT Pub. No.: WO2016/119523
PCT Pub. Date: Aug. 4, 2016

(65) Prior Publication Data
US 2017/0037146 A1    Feb. 9, 2017

(30) Foreign Application Priority Data

Jan. 30, 2015 (CN) .......................... 2015 1 0051280

(51) Int. Cl.
| | | |
|---|---|---|
| *C07K 16/00* | (2006.01) | |
| *A61K 39/00* | (2006.01) | |
| *C07K 16/32* | (2006.01) | |
| *A61K 39/395* | (2006.01) | |
| *C07K 16/30* | (2006.01) | |
| *C12N 15/63* | (2006.01) | |
| *G01N 33/53* | (2006.01) | |

(52) U.S. Cl.
CPC ............ *C07K 16/32* (2013.01); *A61K 39/395* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3061* (2013.01); *C07K 16/3069* (2013.01); *C12N 15/63* (2013.01); *G01N 33/53* (2013.01); *C07K 2317/24* (2013.01); *C07K 2317/54* (2013.01); *C07K 2317/55* (2013.01); *C07K 2317/56* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| 5,545,807 A | * | 8/1996 | Surani ............... A01K 67/0278 424/184.1 |
| 5,661,016 A | * | 8/1997 | Lonberg ............ A01K 67/0278 424/184.1 |
| 2013/0071384 A1 | | 3/2013 | Andya et al. |

FOREIGN PATENT DOCUMENTS

| CN | 102167742 A | 8/2011 |
| CN | 103153339 A | 6/2013 |
| CN | 104530236 | * 4/2015 |
| WO | WO 03/087131 A2 | 10/2003 |
| WO | WO 2004/008099 A2 | 1/2004 |
| WO | WO 2009/123894 A2 | 10/2009 |
| WO | 104530236 A1 | 5/2013 |
| WO | WO 2013/068902 A1 | 5/2013 |

OTHER PUBLICATIONS

Boerner et al., 1991, J.Immunol., 147 (1):86-95) (Year: 1991).*
Vaughan et al., 1996, Nat.Biotech., 14:309-314). (Year: 1996).*
Longer (Nature Biotec, 23, p. 1117-1125, 2005). (Year: 2005).*
International Search Report corresponding to International Application No. PCT/CN2015/096674.
Notice of Reasons of Rejection corresponding to Japanese Application No. 2016-562486 dated Sep. 12, 2017.
Bookman et al, "Evaluation of Monoclonal Humanized Anti-HER2 Antibody, Trastuzumab, in Patients with Recurrent or Refractory Ovarian or Primary Peritoneal Carcinoma with Overexpression of HER2: A Phase II Trial of the Gynecologic Oncology Group", *Journal of Clinical Oncology* 21, (2):283-290 (2003).
Büchler et al, "Therapy for Pancreatic Cancer with a Recombinant Humanized Anti-HER2 Antibody (Herceptin)", *J Gastrointest Surg* 5:139-146 (2001).

(Continued)

*Primary Examiner* — Lei Yao
(74) *Attorney, Agent, or Firm* — Myers Bigel, P.A.

(57) ABSTRACT

The present invention provides a mutated antibody of the fully humanized HER2 antibody GB235-019, wherein the amino acid sequence of the heavy chain variable region and the amino acid sequence of the light chain variable region of the mutated antibody are respectively SEQ ID NO: 10, SEQ ID NO: 2; SEQ ID NO: 11, SEQ ID NO: 2; or SEQ ID NO: 12, SEQ ID NO: 2. The mutated antibody has the ability to specifically bind to human HER2 antigen, similar to the GB235-019 antibody. They can also be used in combination with additional HER2 positive tumor therapeutic agents for treating HER2 positive tumor, weakly positive tumor or negative tumor.

12 Claims, 6 Drawing Sheets
Specification includes a Sequence Listing.

(56) References Cited

OTHER PUBLICATIONS

Owen et al. "Targeting HER2 + breast cancer cells: Lysosomal accumulation of anti-HER2 antibodies is influenced by antibody binding site and conjugation to polymeric nanoparticles", *Journal of Controlled Release* 172:395-404 (2013).
Extended European Search Report corresponding to European Application No. 15879721.7 dated Oct. 12, 2017.
Office Action corresponding to Korean Application No. 2016-7032586 dated Feb. 2, 2018.

\* cited by examiner

SEQUENCE LISTING

<160> NUMBER OF SEQ ID NOS: 34

<210> SEQ ID NO 1
<211> LENGTH: 118
<212> TYPE: PRT
<213> ORGANISM: Artificial
<220> FEATURE:
<223> OTHER INFORMATION: Recombinant antibody heavy chain variable
      sequence

<400> SEQUENCE: 1

Glu Val Gln Leu Val Gln Ser Gly Ala Glu Val Lys Lys Pro Gly Ala
1               5                   10                  15

Pro Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Leu Ser Arg Gly Asp Phe Trp Gly Gln Gly Thr
            100                 105                 110

Leu Val Thr Val Ser Ser
        115

<210> SEQ ID NO 2
<211> LENGTH: 108
<212> TYPE: PRT
<213> ORGANISM: Artificial
<220> FEATURE:
<223> OTHER INFORMATION: Recombinant antibody light chain variable
      region sequence

<400> SEQUENCE: 2

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 3
<211> LENGTH: 354
<212> TYPE: DNA
<213> ORGANISM: Artificial
<220> FEATURE:
<223> OTHER INFORMATION: Recombinant antibody heavy chain variable
      region coding sequence

<400> SEQUENCE: 3

```
gaggtccagc tggtacagtc tggagctgag gtgaagaagc ctggggcccc agtgaaggtc    60
tcctgcaagg cttctggata caccttcacc agctatgata tcaactgggt gcgacaggcc   120
actggacaag gcttgagtg gatgggatgg atgaaccta acagtggtaa cacaggctat    180
```

<p style="padding-left: 1em">[Note: line 3 as printed:]</p>

```
actggacaag gcttgagtg gatgggatgg atgaacccta acagtggtaa cacaggctat   180
gcacagaagt tccagggcag agtcaccatg accaggaaca cctccataag cacagcctac   240
atggagctga gcagcctgag atctgaggac acggccgtgt attactgtgc gcgcggttac   300
tacctgtctc gtggtgattt ctggggtcaa ggtactctgg tgaccgtctc ctca         354

<210> SEQ ID NO 4
<211> LENGTH: 324
<212> TYPE: DNA
<213> ORGANISM: Artificial
<220> FEATURE:
<223> OTHER INFORMATION: Recombinant antibody light chain variable
      region coding sequence

<400> SEQUENCE: 4
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tccctctcac tttcggcgga   300
gggaccaagg tggagatcaa acgt                                           324

<210> SEQ ID NO 5
<211> LENGTH: 330
<212> TYPE: PRT
<213> ORGANISM: Artificial
<220> FEATURE:
<223> OTHER INFORMATION: Recombinant antibody heavy chain constant
      region sequence

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 6
<211> LENGTH: 106
<212> TYPE: PRT
<213> ORGANISM: Artificial
<220> FEATURE:
<223> OTHER INFORMATION: Recombinant antibody light chain constant
      region sequence

<400> SEQUENCE: 6

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 7
<211> LENGTH: 989
<212> TYPE: DNA
<213> ORGANISM: Artificial
<220> FEATURE:
<223> OTHER INFORMATION: Recombinant antibody heavy chain constant
      region coding sequence

<400> SEQUENCE: 7
gcctccacca agggcccatc ggtcttcccc ctggcaccct cctccaagag cacctctggg      60
ggcacagcgg ccctgggctg cctggtcaag gactacttcc ccgaaccggt gacggtgtct     120
tggaactcag gcgccctgac cagcggcgtg cacaccttcc cggctgtcct acagtcctca     180
```

```
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gggtggtcac gtcctcaccg tcctgcacca ggactggctg aatggcaagg    600
agtacaagtg caaggtctcc aacaaagccc tcccagcccc catcgagaaa accatctcca    660
aagccaaagg gcagccccga gaaccacagg tgtacaccct gcccccatcc cgggatgagc    720
tgaccaagaa ccaggtcagc ctgacctgcc tggtcaaagg cttctatccc agcgacatcg    780
ccgtggagtg ggagagcaat gggcagccgg agaacaacta caagaccacg cctcccgtgc    840
tggactccga cggctccttc ttcctctaca gcaagctcac cgtggacaag agcaggtggc    900
agcaggggaa cgtcttctca tgctccgtga tgcatgaggc tctgcacaac cactacacgc    960
agaagagcct ctccctgtct cccggtaaa                                      989

<210> SEQ ID NO 8
<211> LENGTH: 318
<212> TYPE: DNA
<213> ORGANISM: Artificial
<220> FEATURE:
<223> OTHER INFORMATION: Recombinant antibody light chain constant
      region coding sequence

<400> SEQUENCE: 8
actgtggctg caccatctgt cttcatcttc ccgccatctg atgagcagtt gaaatctgga     60
actgcctctg ttgtgtgcct gctgaataac ttctatccca gagaggccaa agtacagtgg    120
aaggtggata acgcccttca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgt                                                  318

<210> SEQ ID NO 9
<211> LENGTH: 1217
<212> TYPE: DNA
<213> ORGANISM: Artificial
<220> FEATURE:
<223> OTHER INFORMATION: Recombinant IgG1 antibody coding sequence

<400> SEQUENCE: 9 gtgggggggcc gggatacaat tgaattcagg aggaatttaa aatgaaaaag acagctatcg     60
cgattgcagt ggcactggct ggtttcgcta ccgtggccca ggcggccgag ctcgacatcc    120
agatgaccca gtctccatct tccgtgtctg catctgtagg agacagagtc accatcactt    180
gtcgggcgag tcagggtatt agcagctggt tagcctggta tcagcagaaa ccagggaaag    240
cccctaagct cctgatctat gctgcatcca gtttgcaaag tggggtccca tcaaggttca    300
gcggcagtgg atctgggaca gatttcactc tcaccatcag cagcctgcag cctgaagatt    360
ttgcaactta ctattgtcaa caggctaaca gtttccctct cactttcggc ggagggacca    420
aggtggagat caaacgttct agaggtgtgg gtggtagcgg cggcggcggc tctggtggtg    480
gtggatccct cgagatggcc gaggtccagc tggtacagtc tggagctgag gtgaagaagc    540
```

```
ctggggcccc agtgaaggtc tcctgcaagg cttctggata caccttcacc agctatgata      600
tcaactgggt gcgacaggcc actggacaag ggcttgagtg gatgggatgg atgaacccta      660
acagtggtaa cacaggctat gcacagaagt tccagggcag agtcaccatg accaggaaca      720
cctccataag cacagcctac atggagctga gcagcctgag atctgaggac acggccgtgt      780
attactgtgc gcgcggttac tacctgtctc gtggtgattt ctggggtcaa ggtactctgg      840
tgaccgtctc ctcaactagt ggccaggccg ccagcacca tcaccatcac catgcgcat       900 acccgtacga cgttccggac tacgcttctt aggagggtgg tggctctgag ggtggcggtt      960
ctgagggtgg cggctctgag ggaggcggtt ccggtggtgg ctctgggttc cggtgatttt     1020
gattatgaaa gatggcaaac gctaataagg gggctatgac cgaaaatgcc gatgaaacgt     1080
gctacagtct gacgctaaag caactgattc tgtcgctact gatacgtgct gctatcgatg     1140
gttcattgct gacgtttcag ctgctaatgg tatgggtgct cactgggtgg taattttggc     1200
tgggctctct aattcga                                                    1217
```

```
<210> SEQ ID NO 10
<211> LENGTH: 118
<212> TYPE: PRT
<213> ORGANISM: Artificial
<220> FEATURE:
<223> OTHER INFORMATION: Humanized antibody heavy chain variable region
      sequence

<400> SEQUENCE: 10

Glu Val Gln Leu Val Gln Ser Gly Ala Glu Val Lys Lys Pro Gly Ala
1               5                   10                  15

Pro Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Leu Ser Arg Gly Asp Phe Trp Gly Gln Gly Thr
            100                 105                 110

Leu Val Thr Val Ser Ser
        115

<210> SEQ ID NO 11
<211> LENGTH: 118
<212> TYPE: PRT
<213> ORGANISM: Artificial
<220> FEATURE:
<223> OTHER INFORMATION: Humanized antibody heavy chain variable region
      sequence

<400> SEQUENCE: 11

Glu Val Gln Leu Val Gln Ser Gly Ala Glu Val Lys Lys Pro Gly Ala
1               5                   10                  15

Pro Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45
```

Gly Trp Met Asn Pro Asn Ser Gly Asn Thr Gly Tyr Ala Gln Lys Phe
        50                  55                  60

Gln Gly Arg Val Thr Met Thr Arg Gln Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Leu Ser Arg Gly Asp Phe Trp Gly Gln Gly Thr
                100                 105                 110

Leu Val Thr Val Ser Ser
        115

<210> SEQ ID NO 12
<211> LENGTH: 118
<212> TYPE: PRT
<213> ORGANISM: Artificial
<220> FEATURE:
<223> OTHER INFORMATION: Humanized antibody heavy chain variable region
      sequence

<400> SEQUENCE: 12

Glu Val Gln Leu Val Gln Ser Gly Ala Glu Val Lys Lys Pro Gly Ala
1               5                   10                  15

Pro Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ala Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Leu Ser Arg Gly Asp Phe Trp Gly Gln Gly Thr
                100                 105                 110

Leu Val Thr Val Ser Ser
        115

<210> SEQ ID NO 13
<211> LENGTH: 354
<212> TYPE: DNA
<213> ORGANISM: Artificial
<220> FEATURE:
<223> OTHER INFORMATION: Humanized antibody heavy chain variable region
      coding sequence

<400> SEQUENCE: 13
gaggtccagc tggtacagtc tggagctgag gtgaagaagc ctggggcccc agtgaaggtc      60
tcctgcaagg cttctggata caccttcacc agctatgata tcaactgggt gcgacaggcc     120
actggacaag gcttgagtg gatgggatgg atgaacccta acagtggtaa cacaggctat      180
gcacagaagt tccagggcag agtcaccatg accagggaca cctccataag cacagcctac     240
atggagctga gcagcctgag atctgaggac acggccgtgt attactgtgc gcgcggttac     300
tacctgtctc gtggtgattt ctggggtcaa ggtactctgg tgaccgtctc ctca           354

<210> SEQ ID NO 14
<211> LENGTH: 354
<212> TYPE: DNA
<213> ORGANISM: Artificial

```
<220> FEATURE:
<223> OTHER INFORMATION: Humanized antibody heavy chain variable region
      coding sequence

<400> SEQUENCE: 14
gaggtccagc tggtacagtc tggagctgag gtgaagaagc ctggggcccc agtgaaggtc      60
tcctgcaagg cttctggata caccttcacc agctatgata tcaactgggt gcgacaggcc     120
actggacaag gcttgagtg gatgggatgg atgaaccta acagtggtaa cacaggctat       180
gcacagaagt tccagggcag agtcaccatg accaggcaga cctccataag cacagcctac     240
atggagctga gcagcctgag atctgaggac acggccgtgt attactgtgc gcgcggttac     300
tacctgtctc gtggtgattt ctggggtcaa ggtactctgg tgaccgtctc ctca           354

<210> SEQ ID NO 15
<211> LENGTH: 354
<212> TYPE: DNA
<213> ORGANISM: Artificial
<220> FEATURE:
<223> OTHER INFORMATION: Humanized antibody heavy chain variable region
      coding sequence

<400> SEQUENCE: 15
gaggtccagc tggtacagtc tggagctgag gtgaagaagc ctggggcccc agtgaaggtc      60
tcctgcaagg cttctggata caccttcacc agctatgata tcaactgggt gcgacaggcc     120
actggacaag gcttgagtg gatgggatgg atgaaccta acagtggtaa cacaggctat       180
gcacagaagt tccagggcag agtcaccatg accaggaaca ccgccataag cacagcctac     240
atggagctga gcagcctgag atctgaggac acggccgtgt attactgtgc gcgcggttac     300
tacctgtctc gtggtgattt ctggggtcaa ggtactctgg tgaccgtctc ctca           354

<210> SEQ ID NO 16
<211> LENGTH: 19
<212> TYPE: PRT
<213> ORGANISM: Artificial
<220> FEATURE:
<223> OTHER INFORMATION: Recombinant antibody signal peptide sequence

<400> SEQUENCE: 16

Met Glu Leu Gly Leu Ser Trp Ile Phe Leu Leu Ala Ile Leu Lys Gly
1               5                   10                  15

Val Gln Cys

<210> SEQ ID NO 17
<211> LENGTH: 57
<212> TYPE: DNA
<213> ORGANISM: Artificial
<220> FEATURE:
<223> OTHER INFORMATION: Recombinant antibody signal peptide coding
      sequence

<400> SEQUENCE: 17
atggagttgg gactgtcttg gatttttctg ttggctattc tgaaaggtgt gcagtgt          57

<210> SEQ ID NO 18
<211> LENGTH: 29
<212> TYPE: DNA
<213> ORGANISM: Artificial
<220> FEATURE:
<223> OTHER INFORMATION: PCR primer sequence

<400> SEQUENCE: 18
```

| | |
|---|---|
| gaattcgcgg ccgcatggag ttgggactg | 29 |

<210> SEQ ID NO 19
<211> LENGTH: 34
<212> TYPE: DNA
<213> ORGANISM: Artificial
<220> FEATURE:
<223> OTHER INFORMATION: PCR primer sequence

<400> SEQUENCE: 19

| | |
|---|---|
| ctgggtcatc tggatgtcac actgcacacc tttc | 34 |

<210> SEQ ID NO 20
<211> LENGTH: 34
<212> TYPE: DNA
<213> ORGANISM: Artificial
<220> FEATURE:
<223> OTHER INFORMATION: PCR primer sequence

<400> SEQUENCE: 20

| | |
|---|---|
| gaaaggtgtg cagtgtgaca tccagatgac ccag | 34 |

<210> SEQ ID NO 21
<211> LENGTH: 36
<212> TYPE: DNA
<213> ORGANISM: Artificial
<220> FEATURE:
<223> OTHER INFORMATION: PCR primer sequence

<400> SEQUENCE: 21

| | |
|---|---|
| gatggtgcag ccacagtacg tttgatctcc accttg | 36 |

<210> SEQ ID NO 22
<211> LENGTH: 26
<212> TYPE: DNA
<213> ORGANISM: Artificial
<220> FEATURE:
<223> OTHER INFORMATION: PCR primer sequence

<400> SEQUENCE: 22

| | |
|---|---|
| atcaaacgta ctgtggctgc accatc | 26 |

<210> SEQ ID NO 23
<211> LENGTH: 33
<212> TYPE: DNA
<213> ORGANISM: Artificial
<220> FEATURE:
<223> OTHER INFORMATION: PCR primer sequence

<400> SEQUENCE: 23

| | |
|---|---|
| gtttaaacgg atccctaaca ctctcccctg ttg | 33 |

<210> SEQ ID NO 24
<211> LENGTH: 32
<212> TYPE: DNA
<213> ORGANISM: Artificial
<220> FEATURE:
<223> OTHER INFORMATION: PCR primer sequence

<400> SEQUENCE: 24

| | |
|---|---|
| gtaccagctg gacctcacac tgcacacctt tc | 32 |

<210> SEQ ID NO 25
<211> LENGTH: 32
<212> TYPE: DNA
<213> ORGANISM: Artificial

```
<220> FEATURE:
<223> OTHER INFORMATION: PCR primer sequence

<400> SEQUENCE: 25
gaaaggtgtg cagtgtgagg tccagctggt ac                                32

<210> SEQ ID NO 26
<211> LENGTH: 35
<212> TYPE: DNA
<213> ORGANISM: Artificial
<220> FEATURE:
<223> OTHER INFORMATION: PCR primer sequence

<400> SEQUENCE: 26
gatgggccct tggtggaggc tgaggagacg gtcac                             35

<210> SEQ ID NO 27
<211> LENGTH: 32
<212> TYPE: DNA
<213> ORGANISM: Artificial
<220> FEATURE:
<223> OTHER INFORMATION: PCR primer sequence

<400> SEQUENCE: 27
accgtctcct cagcctccac caagggccca tc                                32

<210> SEQ ID NO 28
<211> LENGTH: 36
<212> TYPE: DNA
<213> ORGANISM: Artificial
<220> FEATURE:
<223> OTHER INFORMATION: PCR primer sequence

<400> SEQUENCE: 28
gtttaaacgg atcctcattt accgggagac agggag                            36

<210> SEQ ID NO 29
<211> LENGTH: 26
<212> TYPE: DNA
<213> ORGANISM: Artificial
<220> FEATURE:
<223> OTHER INFORMATION: Mutagenesis primer sequence

<400> SEQUENCE: 29
gtcaccatga ccagggacac ctccat                                       26

<210> SEQ ID NO 30
<211> LENGTH: 26
<212> TYPE: DNA
<213> ORGANISM: Artificial
<220> FEATURE:
<223> OTHER INFORMATION: Mutagenesis primer sequence

<400> SEQUENCE: 30
atggaggtgt ccctggtcat ggtgac                                       26

<210> SEQ ID NO 31
<211> LENGTH: 30
<212> TYPE: DNA
<213> ORGANISM: Artificial
<220> FEATURE:
<223> OTHER INFORMATION: Mutagenesis primer sequence

<400> SEQUENCE: 31
gtcaccatga ccaggcagac ctccataagc                                   30
```

```
<210> SEQ ID NO 32
<211> LENGTH: 30
<212> TYPE: DNA
<213> ORGANISM: Artificial
<220> FEATURE:
<223> OTHER INFORMATION: Mutagenesis primer sequence

<400> SEQUENCE: 32
gcttatggag gtctgcctgg tcatggtgac                                        30

<210> SEQ ID NO 33
<211> LENGTH: 27
<212> TYPE: DNA
<213> ORGANISM: Artificial
<220> FEATURE:
<223> OTHER INFORMATION: Mutagenesis primer sequence

<400> SEQUENCE: 33
catgaccagg aacaccgcca taagcac                                           27

<210> SEQ ID NO 34
<211> LENGTH: 27
<212> TYPE: DNA
<213> ORGANISM: Artificial
<220> FEATURE:
<223> OTHER INFORMATION: Mutagenesis primer sequence

<400> SEQUENCE: 34
gtgcttatgg cggtgttcct ggtcatg                                           27
```

MUTATED ANTIBODY OF FULLY HUMANIZED HER2 ANTIBODY, AND ENCODING GENE AND USE THEREOF

RELATED APPLICATIONS

This application is a 35 U.S.C. § 371 national phase application of and claims priority to PCT Application PCT/CN2015/096674 filed Dec. 8, 2015; which claims priority to Chinese Application No. 201510051280.3 filed Jan. 30, 2015. The entire content of each is incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 9363-34_ST25v2.txt, 20,725 bytes in size, generated on Dec. 14, 2016 and filed via EFS-Web, is provided in lieu of a paper copy. The Sequence Listing is incorporated herein by reference into the specification for its disclosures.

TECHNICAL FIELD

The present invention relates to the field of antibody technology, in particularly, the present invention relates to a mutated antibody of a fully human HER2 antibody, and an encoding gene and use thereof.

BACKGROUND OF THE INVENTION

Breast cancer is the most common malignancy in women worldwide. The HER family regulates the growth and development of normal mammary gland, and overexpression of HER2 is associated with breast cancer. Trastuzumab, having the trade name of Herceptin, is the first humanized monoclonal antibody medicament for use in treatment of human epidermal growth factor receptor 2 (HER2) positive metastatic breast cancer. Although Herceptin has become a standard therapeutic regime for HER2 positive malignancies, 40% of patients remain non-responsive to this medicament. Moreover, drug resistance has occurred as a common severe problem in anti-HER2 therapeutic approach. Redundancy of the growth factor and interference among the intracellular signal transduction pathways are believed to be the main reasons that facilitate the drug resistance in breast cancer patients. Pertuzumab, recently developed by Genentech Corporation (USA) together with Roche Corporation, is a novel anti-HER2 humanized antibody. Unlike Herceptin, Pertuzumab targets an antigen epitope which is located in the extracellular region II of the HER2 receptor. Results of clinical experimental studies showed that use of Pertuzumab alone produces a weak anti-tumor therapeutic effect. However, it has been studied to show that use of Pertuzumab in combination with Herceptin can more completely block HER signal tranduction due to complementation of their mechanisms of effect, resulting in more effective inhibition of growth of tumor cells.

Glycosylation modification of protein is a process whereby a specific polysaccharide chain is added onto the protein in endoplasmic reticulum to form an oligosaccharide chain. Glycosylation of protein is site specific, and also enzyme-directed. Depending on the mode of linkage to the protein moiety, glycosylation modification of protein can either be O-linked or N-linked, in which the conservative N-glycosylation site being Asn-X-Thr/Ser, wherein X is any amino acid other than Pro. There is a conservative N-linked glycosylation site Asn297 within the CH2 region in the Fe segment of the heavy chain of human IgG. The Fe polysaccharide chain is essential for optimal binding of an antibody to various receptors, effective elimination of pathogens by the antibody, as well as control of clinical properties of a therapeutic antibody. N-glycosylation modification of human IgG Fab may have an obvious promoting or inhibitory effect on the function of binding of an antibody to an antigen. Minor changes in the position where glycosylation modification occurs may produce a completely different effect on subsequent processing of polysaccharide chain and binding activity of an antibody to an antigen.

The present applicant previously obtained a fully human anti-human HER2 (Her-2/neu) monoclonal antibody GB235-019 by using fully human scFV phage library screening technology and genetic engineering recombination expression technology (reference can be made to the Chinese Patent Application No. 201410705404.0). The monoclonal antibody can reduce transfusion reaction and immunogenicity, increase drug safety, and presents a better pharmacokinetic profile. Moreover, GB235-019 can be used in combination with other HER2 positive tumor therapeutic agents to treat HER2 positive tumors.

SUMMARY OF THE INVENTION

The present invention provides a mutated antibody of the fully human HER2 antibody GB235-019, wherein the amino acid sequence of the heavy chain variable region and that of the light chain variable region of the mutated antibody are respectively SEQ ID NO:10, SEQ ID NO:2; SEQ ID NO:11, SEQ ID NO:2; or SEQ ID NO:12, SEQ ID NO:2.

In an embodiment, the mutated antibody of the fully human HER2 antibody GB235-019 of the present invention is in the form of Fab, Fab', F(ab') 2, Fv or scFv. The Fab, Fab', F(ab') 2, Fv or scFv has the meaning commonly known in the art.

In an embodiment, the mutated antibody of the fully human HER2 antibody GB235-019 of the present invention described above may further comprise the heavy chain constant region and light chain constant region of human IgG. In a particular embodiment, the human IgG is IgG1. In a particular embodiment, the amino acid sequence of the human IgG heavy chain constant region is SEQ ID NO:5, and the amino acid sequence of the human IgG light chain constant region is SEQ ID NO:6.

The present invention provides a nucleotide sequence encoding the mutated antibody of the fully human HER2 antibody GB235-019 of the present invention.

In a particular embodiment, the nucleotide sequence encoding the heavy chain variable region having the amino acid sequence of SEQ ID NO:10 is SEQ D NO:13, the nucleotide sequence encoding the heavy chain variable region having the amino acid sequence of SEQ ID NO:11 is SEQ ID NO:14, the nucleotide sequence encoding the heavy chain variable region having the amino acid sequence of SEQ ID NO:12 is SEQ ID NO:15, and the nucleotide sequence encoding the light chain variable region having the amino acid sequence of SEQ ID NO:2 is SEQ ID NO:4.

In a particular embodiment, when the mutated antibody of the fully human HER2 antibody GB235-019 of the present invention is a full-length antibody, in the nucleotide sequence of the present invention, the nucleotide sequence encoding the heavy chain constant region is SEQ ID NO:7, and the nucleotide sequence encoding the light chain constant region is SEQ NO:8.

The present invention provides an expression vector in which the nucleotide sequence of the present invention is operably linked to the expression control sequence of the expression vector. In particular embodiments, the expression vector is pGEM-T vector or 293 vector.

The present invention provides cells which comprise the expression vector of the present invention. The cells can either be prokaryotic or eukaryotic. In particular embodiments, the cells can be mammal cells, such as FreeStyle 293F cells.

The present invention provides a pharmaceutical composition comprising the mutated antibody of the fully human HER2 antibody GB235-019 of the present invention and a pharmaceutically acceptable carrier.

The present invention provides a combined medicament, comprising the mutated antibody of the fully human HER2 antibody GB235-019 of the present invention and additional HER2 positive tumor therapeutic agent(s), the HER2 positive tumor therapeutic agent(s) being Herceptin and/or Pertuzumab. The combined medicament can be administered to a subject in the following amounts: 0.001 to 500 mg/kg of the mutated antibody of GB235-019+0.001 to 500 mg/kg of Herceptin and/or Pertuzumab; 0.001 to 300 mg/kg of the mutated antibody of GB235-019+0.001 to 300 mg/kg of Herceptin and/or Pertuzumab; 0.001 to 200 mg/kg of the mutated antibody of GB235-019+0.001 to 200 mg/kg of Herceptin and/or Pertuzumab; 0.01 to 200 mg/kg of the mutated antibody of GB235-019+0.01 to 200 mg/kg of Herceptin and/or Pertuzumab; 0.01 to 100 mg/kg of the mutated antibody of GB235-019+0.01 to 100 mg/kg of Herceptin and/or Pertuzumab; 0.1 to 90 mg/kg of the mutated antibody of GB235-019+0.1 to 90 mg/kg of Herceptin and/or Pertuzumab; 0.1 to 70 mg/kg of the mutated antibody of GB235-019+0.1 to 70 mg/kg of Herceptin and/or Pertuzumab: 0.1 to 60 mg/kg of the mutated antibody of GB235-019+0.1 to 60 mg/kg of Herceptin and/or Pertuzumab; 0.1 to 50 mg/kg of the mutated antibody of GB235-019+0.1 to 50 mg/kg of Herceptin and/or Pertuzumab; 0.1 to 40 mg/kg of the mutated antibody of GB235-019+0.1 to 40 mg/kg of Herceptin and/or Pertuzumab; 1 to 40 mg/kg of the mutated antibody of GB235-019+1 to 40 mg/kg of Herceptin and/or Pertuzumab. The mutated antibody of the fully human HER2 antibody GB235-019 of the present invention can be administered to the subject separately or simultaneously with additional HER2 positive tumor therapeutic agent(s). The administration routes can be those commonly used in the art for antibodies.

The present invention provides a kit comprising the mutated antibody of the fully human HER2 antibody GB235-019 of the present invention. The kit can be used to detect HER2 protein, in a sample. The kit can further comprise additional components commonly used in the kits for detecting HER2 in the art.

The present invention provides use of the mutated antibody of the fully human HER2 antibody GB235-019 of the present invention for the preparation of a medicament useful for treating an HER2 positive tumor, weakly positive tumor or negative tumor in a subject.

The term "HER2 positive tumor" means that if the result of IHC (immunohistochemistry) assay is three plus signs (+++), that is, more than 30% of the tumor cells exhibit complete and strong staining in the cytoplasmic membrane, then HER2 positive is indicated; and if the result is two plus signs (++), that is, at least 10% of the tumor cells exhibit weakly to moderately complete staining in the cytoplasmic membrane, then FISH (fluorescence in-situ hybridization) or CISH (chromogenic in-situ hybridization) assay is further performed, and if the result is positive (gene amplication occurs), then HER2 positive can be diagnosed. Preferably, the assay result of HER2 positive tumor is a result obtained using a detection kit (IHC, FISH or CISH assay kit) accredited by China Food and Drug Administration. How to determine whether a tumor is HER2 positive tumor is well known within a practicing physician.

the term "HER2 weakly positive tumor" means that if the result of IHC assay is two plus signs (++), that is, at least 10% of the tumor cells exhibit weakly to moderately complete staining in the cytoplasmic membrane, then FISH or CISH assay is further performed, and if no gene amplication occurs, then HER2 weakly positive is indicated. Correspondingly, "HER2 negative tumor" means that if the result of IHC assay is one plus sign (+) or 0, then HER2 negative is indicated.

The HER2 positive tumor can be selected from HER2 positive breast cancer, gastric cancer, lung cancer, non-small cell lung cancer, bone cancer, pancreatic cancer, skin cancer, head or neck cancer, cutaneous or intraocular melanoma, uterine cancer, ovary cancer, rectal cancer, anal cancer, colon cancer, fallopian tube cancer, endometrial cancer, cervical cancer, vaginal cancer, vulvar cancer, Hodgkin's disease, esophageal cancer, small intestine cancer, endocrine system cancer, thyroid cancer, parathyroid cancer, adrenal gland cancer, soft tissue cancer, urethra cancer, penis cancer, prostate cancer, bladder cancer, kidney or urethra cancer, kidney cell cancer, renal pelvis cancer, mesothelioma, liver cell cancer, gallbladder cancer, chronic or acute leukemia, lymphatic cell lymphoma, central nerve system (CNS) cancer, spinal tumor, neuroglioma of brain stem, glioblastoma multiforme, astrocytoma, neurilemmoma, ependymoma, medulloblastoma, meningioma, squamous cell carcinoma and pituitary adenoma.

Preferably, the subject is a human.

BRIEF DESCRIPTION OF THE DRAWINGS

FIG. 5A shows that the measured molecular weight of the heavy chain of GB235-019N73D mutated antibody was consistent with the theoretical molecular weight, indicating absence of glycosylation in the heavy chain. FIG. 5B and FIG. 5C show that the measured molecular weight of the heavy chain of mutated antibodies GB235-019N73Q and GB235-019S75A was closely consistent with the theoretical molecular weight (with difference <1 Da), indicating that the N-glycosylation site in the Fab framework region had been removed.

019N73D mutated antibody was similar to that of GB235-019WT antibody. Pertuzumab also completely inhibited upregulation of HER3 phosphorylation in the BT-474 cells induced by Heregulin-α. The inhibitory effect of Herceptin on upregulation of HER3 phosphorylation in the BT-474 cells induced by Heregulin-α is also significant. And, separately administered (GB235-019WT antibody and GB235-019N73D mutated antibody did not inhibit upregulation of Akt phosphorylation induced by Heregulin-α, whereas Pertuzumab significantly inhibited upregulation of Akt phosphorylation by Heregulin-α so induced. Separately administered GB235-019N73D mutated antibody and GB235-019WT antibody significantly inhibited upregulation of ERK1/2 phosphorylation induced by Heregulin-α. The efficacy of GB235-019N73D mutated antibody is similar to that of GB235-019WT antibody.

Figure 9:
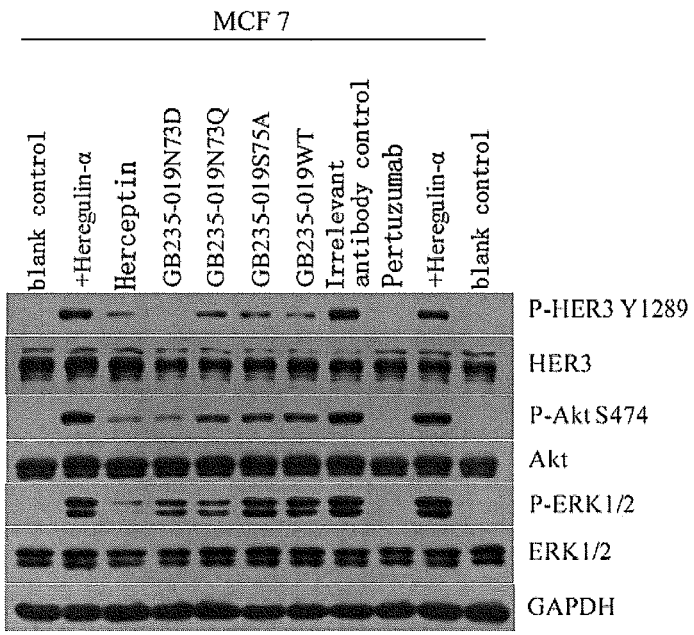

FIG. 9 shows the inhibitory effect of the recombinant full-length anti-human HER2 antibodies on breast cancer MCF 7 cell signal transduction. HER2 negative MCF 7 breast cancer cells expressing a low level of HER2 and a high level of HER3 but not expressing P-HER2 and P-HER3 were subjected to starvation culture in 0.1% fetal bovine serum medium for 24 hours. Then 20 µg/ml of each of the GB235-019WT antibody and the mutated antibodies GB235-019N73D, GB235-019N73Q, and GB235-019S75A were added, and 20 µg/ml of Herceptin and 20 µg/ml of Pertuzumab were separately administered. After treating the MCF 7 cells with the antibodies for 6 hours, Heregulin-α at a final concentration of 100 ng/ml was added to induce for 10 minutes, at which time samples were taken. Cell lysates were subjected to immunoblotting, and the whole and the phosphorylated HER3, Akt and ERK were detected respectively using corresponding antibodies. The results in FIG. 9 show that, compared with the control group without addition of Heregulin-α, Heregulin-α induced upregulation of HER3 phosphorylation in the MCF 7 cells, Separately administered GB235-019WT antibody and the mutated antibodies GB235-019N73D, GB235-019N73Q GB235-019S75A significantly inhibited upregulation of HER3 phosphorylation in the MCF 7 cells induced by Heregulin-α. Separately administered Herceptin and Pertuzumab also significantly inhibited upregulation of HER3 phosphorylation in the MCF 7 cells by induced Heregulin-α. Separately administered GB235-019WT antibody and the mutated antibodies GB235-019N73D, GB235-019N73Q, GB235-019S75A significantly inhibited upregulation of Akt phosphorylation induced by Heregulin-α, and separately administered Pertuzumab completely reversed upregulation of Akt phosphorylation induced by Heregulin-α. Separately administered the mutated antibodies GB235-019N73D and GB235-019N73Q significantly inhibited upregulation of ERK1/2 phosphorylation in the MCF 7 cells induced by Heregulin-α, and separately administered (GB235-019WT antibody and GB235-019S75A mutated antibody weakly inhibited upregulation of ERK1/2 phosphorylation induced by Heregulin-α. Separately administered Pertuzumab completely reversed upregulation of ERK1/2 phosphorylation induced by Heregulin-α.

Figure 10:
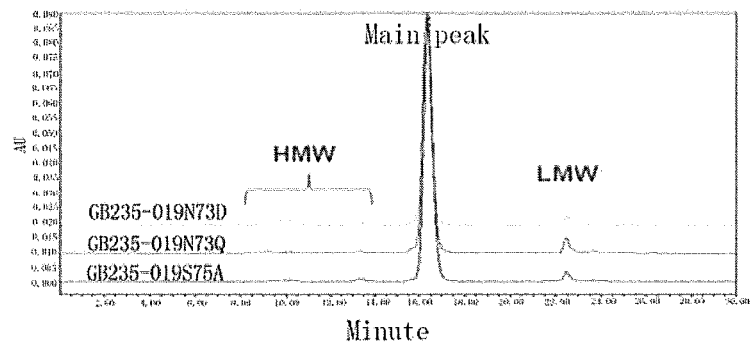

FIG. 10 shows the chromatograms of molecular size exclusion chromatography of the three mutated antibodies GB235-019N73D, GB235-019N73Q and GB235-019S75A. 30 µg of each of the three mutated antibodies was subjected to molecular exclusion chromatography (SEC-HPLC) to determine their respective purity. The purity of the main peak of the GB235-019N73D antibody was 88.3%, that of the GB235-019N73Q antibody was 89.7%, and that of the GB235-019S75A antibody was 93.1%.

Figure 11:
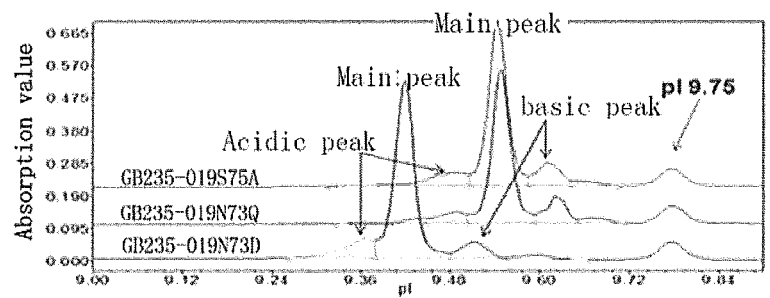

FIG. 11 shows the electrophoregrams of imaging capillary isoelectric focusing electrophoresis of the three mutated antibodies GB235-019N73D, GB235-019N73Q and GB235-019S75A. The three mutated antibodies were respectively subjected to imaging capillary isoelectric focusing (iCIEF) to determine the isoelectric point (pI) of the respective main peaks and the purity of the charge isomers. The three mutated antibodies all had a relatively high measured isoelectric point, which was in the range of 9.4 to 9.6. The isoelectric point of GB235-019N73D was about 0.1 lower than that of GB235-019N73Q and GB235-019S75A, and its main peak purity was relatively the highest.

Figure 12:
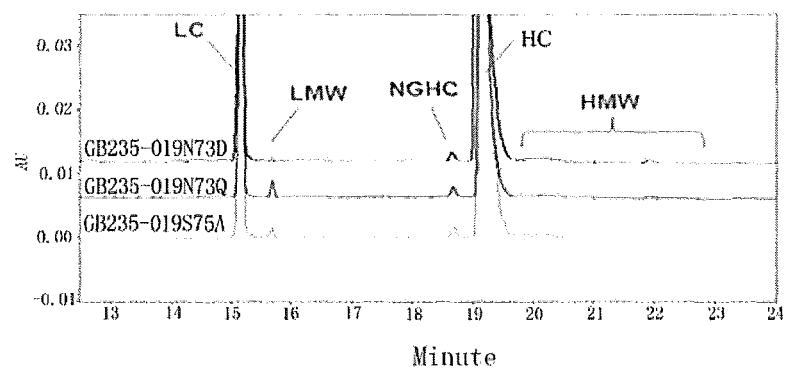

FIG. 12 shows the electrophoregrams of reducing capillary gel electrophoresis of the three mutated antibodies GB235-019N73D, GB235-019N73Q and GB235-019S75A. The three mutated antibodies were respectively subjected to reducing capillary gel electrophoresis analysis (rCE-SDS) to determine their respective purity (the sum of the percentage of the light chain and the heavy chain). The three mutated antibodies all had certain impurities of low molecular weight and high molecular weight. GB235-019N73D had relatively the least impurity content, and its purity in terms of the sum of the light chain and the heavy chain (LC +HC) was the highest.

Figure 13:
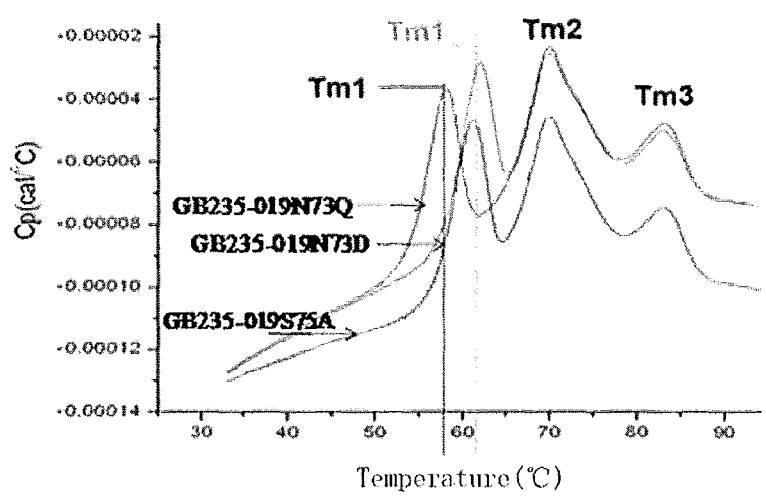

FIG. 13 shows the differential scanning calorimetry diagrams of the three mutated antibodies GB235-019N73D, GB235-019N73Q and GB235-019S75A. The three mutated antibodies were respectively subjected to differential scanning calorimetry (DSC) to determine the respective Tm value (phase transition temperature, which means that 50% of the biological molecules were in an unfolded state at that temperature). The Tm1 of the three molecules are different from one another. The Tm1 of GB235-019N73Q was relatively the lowest, while that of GB235-019N73Q was close to that of GB235-019S75A. The higher the Tm value, the better the thermal stability. The difference in Tm1 indicates to some extent that the mutation has some effect on the CH2 domain. GB235-019N73D and GB235-019S75A had a better thermal stability than GB235-019N73Q.

DETAILED DESCRIPTION OF THE INVENTION

The technical solutions of the present invention will be further illustrated by the following particular examples; but the present invention is not limited thereto.

Example 1

Screening Clones that Specifically Bound to Human HER2-Fc From Fully Human scFV Phage Library Taking advantage of the specificity of antigen-antibody binding of ELISA technology, human HER2 (extracellular domain)-Fc fusion protein (abbreviated as hHER2-Fc) antigen was coated onto an ELISA plate, and phages specifically attached to the coated antigen were washed and panned. The human HER2-Fc (purchased from Sino Biological Inc., catalog number 10004-H02H) antigen was diluted with PBS (0.01 M $Na_2HPO_4 \cdot 12H_2O$+0.002 M $KH_2PO_4$+0.14 M NaCl+0.002 M KCl, pH=8.6) to 5 µg/ml, added to the ELISA plate at 100 µl/well, and coated at 4° C. overnight. The plate was washed with PBST (PBS buffer containing 0.05% Tween 20) for 4 times, then 5% BSA (purchased from Amresco Inc., USA, catalog number: 0332-100 g, the solution being PBS) was added at 300 µl/well to perform blocking at 37° C. for 1 hour. The plate was washed again with PBST twice. A suspension of a fully human scFv phage antibody library (which was constructed by EUREKA (Beijing) Biotechnology Ltd. by combining antibody variable region genes from lymphatic cells from a multiple of healthy individuals with artificially synthesized heavy chain CDR3 gene) containing $7 \times 10^{10}$ independent clones was added to the ELISA plate at 100 μl/well, and incubation was performed at 37° C. for 2 hours. After incubation ended, the phage suspension in the wells of the ELISA plate was aspirated. Then PBST was added to each well at 300 μl/well, and the content in the wells was thoroughly blown for 5 minutes to remove the phages that were not specifically bound to the coated antigen. 0.2 M glycine-HCl (pH=2.2) eluant containing 0.1%BSA (purchased from Amresco Inc., USA, catalog number: 0332-100 g, the solution being PBS) was added to perform incubation at room temperature for 10 minutes. Then the content in the wells was thoroughly blown to elute the phages that were specifically attached to the coated antigen. The eluted phage suspension was neutralized with 1 M Tris-HCl (pH 9.1) buffer. The eluted phages were added to 1 mL of bacteria TG1 (Lucigen Inc., USA, Catalog number 60500-0) growing in log phase (as indicated by OD600 being about 0.3 to 0.4), and the resulting bacterial solution was left standing at 37° C. for 1 hour for infection. 10 μl of the infected bacterial solution was subjected to 10-fold serial dilution, and the 10-fold, 100-fold and 1000-fold dilutions were plated and counted. 90 μl of the infected bacterial solution was stored in glycerine at a final concentration of glycerine of 10% at −80° C. The remaining infected bacterial solution was all plated onto a 150 mm 2×YT-A solid plate (17 g/L of tryptone, 10 g/L of yeast extract, 5 g/L of sodium chloride, 15 g/L of agar and 100 μg/ml of ampicillin) and cultured at 37° C. overnight. 5 ml of 2×YT-A-10% glycerine medium was added to the 150 mm plate for overnight. The plate was gently scraped using a sterile spreading rod until no residual bacterial solution was present on the plate. In the second round of amplification, a suitable amount of scraped bacterial solution was added to 5 ml of 2×YT-AMP-glucose liquid medium (17 g/L of tryptone, 10 g/L of yeast extract, 5 g/L of sodium chloride, 2% of glucose and 100 μm/ml of ampicillin) (OD600 desirably being about 0.05 to 0.1), and cultured at 37° C., 200 rpm until log phase (OD600 being about 0.3 to 0.4). Then M13K07 helper phage (purchased from NEB Inc., USA, catalog, number: N0315S) in an amount of 20 times the total number of the bacteria was added to perform infection at 37° C. for 1 hour. After infection, bacteria pellet collected at 1500 g for 5 minutes was resuspended in 2×YT-AMP-Kana medium (17 g/L of tryptone, 10 g/L of yeast extract, 5 g/L of sodium chloride, 50 μg/ml of kanamycin and 100 μg/ml of ampicillin), and cultured at 30° C., 200 rpm overnight to complete the amplification and preparation of recombinant phages. A second round of panning and a third round of amplification and panning were conducted in the same manner. Bacterial colonies were picked to 5 ml 2×YT-AMP-glucose liquid medium (17 g/L of tryptone, 10 g/L of yeast extract, 5 g/L of sodium chloride, 2% of glucose and 100 μg/ml of ampicillin) and cultured at 37° C., 200 rpm overnight. Plasmids were extracted using a plasmid extraction kit (purchased from Qiagen Inc., USA, catalog number: 12943), identified by sequencing, and stored at −80° C.

Example 2

Identifying the Immunoreactivity of the Phages that Specifically Bound to Human HER2-Fc Using Enzyme-Linked Immunosorbent Assay (ELISA)

Using enzyme-linked immunosorbent assay (ELISA), the immunoreactivity of the phages obtained in Example 1 that specifically bound to human HER2-Fc was further identified. Human HER2-Fc antigen (purchased from Sino Biological Inc., catalog number: 10004-H02H) was diluted with PBS (pH=8.6) to 2 μg/ml, added to an ELISA plate at 100 μl/well to perform coating at 4° C. overnight. The plate was washed with PBST for four times, then 5% BSA (purchased from Amresco, USA, catalog number: 0332-100 g, the solution being PBS) was added at 300 μl/well to perform blocking at 37° C. for 1 hour. The plate was again washed with PBST twice, then suspensions of the phage clones were added at 100 μl/well to perform incubation at 37° C. for 2 hours. The plate was washed with PBST for four times. HRP-labeled anti-M13K07 phage antibodies (purchased from GE Inc., USA. catalog number 27-9421-01, 1:5000 dilution with PBST, 100 μl/well) were added to perform incubation at room temperature for 1 hour. The plate was washed with PBST for four times, then a solution of the soluble single component substrate 3,3',5,5'-tetramethylbenzidine (purchased from Tiangen Co., Ltd. catalog number: PA107-01) was added at 100 μl/well to perform incubation at room temperature for 15 minutes for visualization. A stop solution (1 M sulfuric acid) was added at 50 μl/well, and absorbance value was read at 450/570 nm wavelength on a multi-functional ELISA plate (Bio-Rad, Model 680 Micro reader, USA).

Results indicated that after three rounds of repetitive screening, a total of 1312 scFV phage clones that could bind to human HER2-Fc antigen were obtained, among which 499 clones of scFV phage could specifically bind to human HER2-Fc antigen. DNA sequencing revealed that 102 scFvs were different both in DNA sequences and amino acid sequences among these clones (as shown in Table 1).

TABLE 1

| Number of clones obtained by screening that could bind to HER2-Fc | Number of clones that could specifically bind to human HER2-Fc | Number of clones that could specifically bind to human HER2-Fc and that had unique nucleotide sequence |
| --- | --- | --- |
| 1312 | 499 | 102 |

Example 3

Detecting Interspecies Cross Reactivity, and Intermolecular Cross Reactivity Among HER Family Members, of the 102 Human HER2-Fc-Specific scFvs Using ELISA Interspecies cross reactivity, and intermolecular cross reactivity among HER family members, of the 102 human HER2-Fc-specific scFvs were detected using ELISA. The same procedure as in Example 2 was followed, except that the human HER2-Fc antigen for coating was replaced by monkey HER2-Fc (purchased from Sino Biological Inc., catalog number: 90295-C02H), mouse HER2-Fc (purchased from Sino Biological Inc., catalog number: 50714-M02H), human HER1-Fc (purchased from Sino Biological Inc., catalog number: 10001-H02H), human HER3-Fc (purchased from Sino Biological Inc., catalog number: 10201-H05H) and human HER4-Fc (purchased from Sino Biological Inc., catalog number: 10363-H02H). The respective antigens were diluted with PBS (pH:=8.6) to 2 μg/ml, and added to an ELISA plate at 100 μl/well to perform coating at 4° C. overnight. The plate was washed with PBST for four times, then 5% BSA (purchased from Amresco, USA, catalog number: 0332-100 g, the solution being PBS) was added at 300 μl/well to perform blocking at 37° C. for 1 hour. The plate was again washed with PBST twice, then suspensions of the 102 clones of the ScFv phage were added at 100 μl/well to perform incubation at 37° C. for 2 hours. The plate was washed with PBST for four times. HRP-labeled anti-M13K07 phage antibodies (purchased from GE Inc., USA, catalog number: 27-9421-01, 1:5000 dilution with PBST, 100 μl/well) were added to perform incubation at room temperature for 1 hour. The plate was washed with PBST for four times, then a solution of the soluble single component substrate 3,3',5,5'-tetramethylbenzidine (purchased from Tiangen Co., Ltd., catalog number: PA107-01) was added at 100 μl/well to perform incubation at room temperature for 15 minutes for visualization. A stop solution (1 M sulfuric acid) was added at 50 μl/well, and absorbance value was read at 450/570 nm wavelength on a multi-functional ELISA plate (Bio-Rad, Model 680 Micro reader, USA).

Results indicated that 96 clones of ScFv phage had cross reactivity to monkey HER2-Fc, and 20 clones had cross reactivity to mouse HER2-Fc. None of the 102 clones had cross reactivity to human HER1-Fc, human HER3-Fc and human HER4-Fe (as shown in Table 2).

TABLE 2

| | Antigen | | | | |
|---|---|---|---|---|---|
| | HER2-Fc | mouse HER2-Fc | human HER1-Fc | human HER3-Fc | human HER4-Fc |
| Number of clones | 96 | 20 | 0 | 0 | 0 |

Example 4

Affinity Ranking of the 102 Clones of ScFv Phage

Affinity ranking of the 102 clones of ScFv phage was performed by ELISA. Human HER2-Fc antigen beginning with 25 μg/ml was subjected to 10-fold dilution with PBS buffer to obtain 8 concentration gradients. The dilutions were respectively incubated with 102 clones of the ScFv phage at room temperature for 4 hours to reach equilibrium. Then the resulting mixtures were added to an ELISA plate previously coated with 2 μg/ml human HER2-Fc antigen (pH=8.6 PBS, 4° C. overnight, 100 μl/well), and the ELISA plate was blocked using 5% BSA (purchased from Amresco Inc., USA, catalog number: 0332-100 g, the solution being PBS) to bind the ScFv antibodies not having been captured. HRP-labeled anti-M13 phage antibodies (purchased from GE Inc., USA, catalog number: 27-9421-01, 1:5000 dilution with PBST, 100 μl/well) were added, and detection was conducted in the same procedure as in Example 2. Affinity ranking of the 102 positive clones was performed in terms of IC50 value (the lower the IC50 value, the higher the affinity).

Results revealed the range of distribution of IC50 value of the 102 clones of ScFv phage, among which 4 clones had an affinity higher than that of Herceptin.

TABLE 3

| | IC50(nM) | | | | |
|---|---|---|---|---|---|
| | ≤2.0 | 2.0-10.0 | 10.0-100.0 | >100.0 | Not detected |
| Number of clones | 4 | 21 | 37 | 25 | 15 |

Example 5

Construction of the Eukaryotic Expression Vector for the GB235-019 Recombinant Full-Length IgG1 Isotype Antibody The eukaryotic expression vector for the recombinant full-length IgG1 isotype antibody GB235-019 (the recombinant full-length antibody sequence 019 clone was designated as GB235-019) was constructed from the 102 clone sequences of ScFv phage. The nucleotide sequence of WG1-019 single-chain antibody clone obtained by screening from fully human ScFv phage library (the single chain antibody sequence clone obtained by screening from the ScPv phage library was designated as WG1-019) was SEQ ID NO:9, comprising a heavy chain variable region and a light chain variable region having the nucleotide sequences of SEQ ID NO:3 (which encoding the amino acid sequence of SEQ ID NO:1) and SEQ ID NO:4 (which encoding the amino acid sequence of SEQ ID NO:2) respectively. The signal peptide had the amino acid sequence of MELGLSWIFLLAILK-GVQC (SEQ ID NO:16) and the nucleotide sequence of ATGGAGTTGGGACTGTCTTGGATTTTCCTGTTGGC-TATTCTGAAAGGTGTGCAGT GT (SEQ ID NO:17) (synthesized by Shanghai Generay Biotech Co, Ltd).

The GB235-019 recombinant full-length antibody had a heavy chain constant region and a light chain constant region which respectively had the nucleotide sequences of SEQ ID NO:7 (which encoding the amino acid sequence of SEQ ID NO:5 and SEQ NO:8 (which encoding the amino acid sequence of SEQ ID NO:6) (synthesized by Shanghai Generay Biotech Co, Ltd).

Primers were designed for constructing the eukaryotic expression vector for the heavy chain and the light chain of the GB235-019 recombinant full-length IgG1 isotype antibody, the primers being as follows:

```
1-1:
5'-GAATTCGCGGCCGCATGGAGTTGGGACTG-3'
(SEQ ID NO: 18)

2-3:
5'-CTGGGTCATCTGGATGTCACACTGCACACCTTTC-3'
(SEQ ID NO: 19)

3-3:
5'-GAAAGGTGTGCAGTGTGACATCCAGATGACCCAG-3'
(SEQ ID NO: 20)

4-4:
5'-GATGGTGCAGCCACAGTACGTTTGATCTCCACCTT
(SEQ ID NO: 21)

G-3'

5-2:
5'-ATCAAACGTACTGTGGCTGCACCATC-3'
(SEQ ID NO: 22)
```

```
-continued
6-1:
5'-GTTTAAACGGATCCCTAACACTCTCCCCTGTTG-3'
(SEQ ID NO: 23)

7-7:
5'-GTACCAGCTGGACCTCACACTGCACACCTTTC-3'
(SEQ ID NO: 24)

8-7:
5'-GAAAGGTGTGCAGTGTGAGGTCCAGCTGGTAC-3'
(SEQ ID NO: 25)

9-1:
5'-GATGGGCCCTTGGTGGAGGCTGAGGAGACGGTCA

C-3' (SEQ ID NO: 26)

10-1:
5'-ACCGTCTCCTCAGCCTCCACCAAGGGCCCATC-3'
(SEQ ID NO: 27)

11-1:
5'-GTTTAAACGGATCCTCATTTACCGGGAGACAGGGA

G-3' (SEQ ID NO: 28)
```

Using the synthesized signal peptide sequence as template, and 1-1 and 2-3 as primers, a gene fragment comprising EcoR I restriction site was obtained through amplification by PCR method and designated as "SPL-GB235-019"; using the synthesized light chain variable region sequence SEQ ID NO:4 as template, and 3-3 and 4-4 as primers, a light chain variable region gene fragment was obtained through amplification by PCR method and designated as "VL-GB235-019"; and using the synthesized light chain constant region sequence SEQ ID NO:8 as template, and 5-2 and 6-1 as primers, a heavy chain constant region gene fragment comprising TGA stop codon and BamH 1 restriction site was obtained through amplification by PCR method and designated as "CL-GB235-019". Using SPL-GB235-19, VL-GB235-019, and CL-GB235-019 gene fragments as templates, and 1-1 and 6-1 as primers, a light chain full-length gene fragment of the GB235-019 antibody was obtained through amplification by over-lapping PCR method (Higuchi R, et al. A general method of in vitro preparation and specific mutagenesis of DNA fragments: study of protein and DNA interactions. Nucleic Acids Research, 1988, 16(15):7351-67).

Likewise, using the synthesized signal peptide sequence as template, and 1-1 and 7-7 as primers, a gene fragment comprising EcoR I restriction site was obtained through amplification by PCR (polymerase chain reaction) method and designated as "SPH-GB235-019"; using the synthesized heavy chain variable region sequence SEQ ID NO:3 as template, and 8-7 and 9-1 as primers, a heavy chain variable region gene fragment was obtained through amplification by PCR method and designated as "VH-GB235-019", and using the synthesized heavy chain constant region sequence SEQ ID NO:7 as template, and 10-1 and 11-1 as primers, a heavy chain constant region gene fragment comprising TGA stop codon and BamH I restriction site was obtained through amplification by PCR method and designated as "CH-GB235-019". Using SPH-GB235-019, VH-GB235-019, and CH-GB235-019 gene fragments as templates, and 1-1 and 11-1 as primers, a heavy chain full-length gene fragment of the GB235-019 antibody was obtained through amplification by over-lapping PCR method.

The above-said heavy chain and light chain full-length gene fragments were cloned to pGEM-T vector (purchased from Promega Inc., USA, catalog number: A3600), such that the 5'-end of the gene fragments comprised EcoR I restriction site and the 3'-end of the fragments comprised TGA stop codon and BamH I restriction site. After DNA sequencing, the clones having been sequenced to be correct were double digested using EcoR I (purchased from NEB Inc., USA. catalog number: R0101S) and BamH I (purchased from NEB Inc., USA, catalog number: R0136S) at 37° C. for 4 hours to recover the gene fragments of interest. The antibody heavy chain full-length gene fragment and light chain full-length gene fragment obtained by the above-said digestion were cloned to 293 vector (purchased from Invitrogen Inc., USA, catalog number: K8300-01). After identification by DNA sequencing, clones comprising the successfully constructed full-length antibody heavy chain eukaryotic expression vector or full-length antibody light chain eukaryotic expression vector were obtained.

Figure 1A:
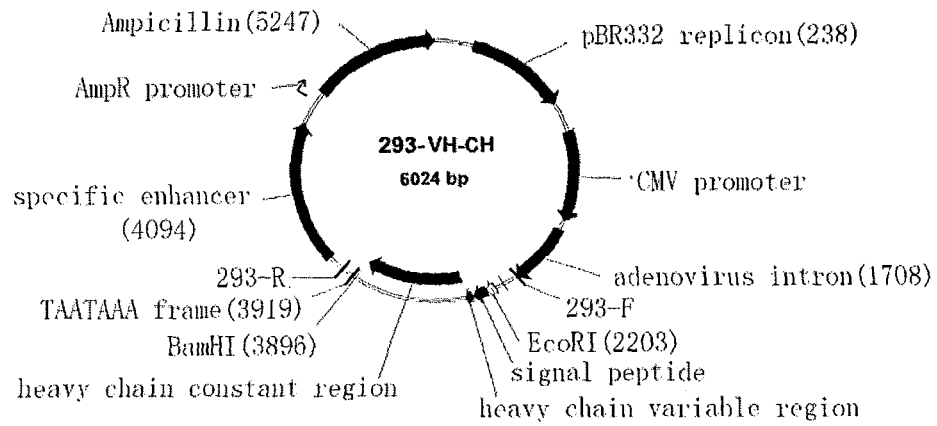
FIG. 1A shows a diagram of structure of the heavy chain expression vector (293-VH-CH) of the recombinant full-length anti-human HER2 antibody GB235-019.
Figure 1B:
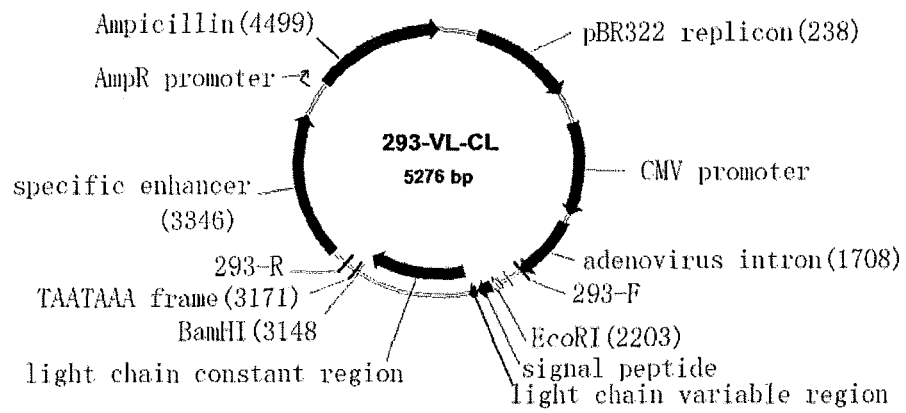
FIG. 1B shows a diagram of structure of the light chain expression vector (293-VL-CL) of the recombinant full-length anti-human HER2 antibody GB235-019. A signal peptide gene fragment comprising 5'-end EcoR1 restriction site, a heavy chain variable region (VH) gene fragment and a heavy chain constant region (CH) gene fragment comprising TGA terminator cadon and 3'-end BamH I restriction site were obtained by PCR method using corresponding templates and primers, respectively (see Example 5 for details), and the three fragments were linked by over-lapping PCR method to obtain the heavy chain full-length gene fragment of the GB235-019 antibody. By the same approach, the light chain full-length gene fragment of the GB235-019 antibody comprising a signal peptide, a light chain variable region (VL) and a light chain constant region (CL) was obtained. The heavy chain full-length gene fragment and the light chain full-length gene fragment were respectively cloned into a pGEM-T vector using the cohesive end formed by restriction enzyme digestion with EcoR I and BamH I.

FIG. 1A shows diagram of structure of the recombinant full-length anti-human HER2 antibody heavy chain (293-VH-CH) expression vector; and FIG. 1B shows diagram of structure of the recombinant full-length anti-human HER2 antibody light chain (293-VL-CL) expression vector.

Example 6

Transient Transfection Expression of the GB235-019 Antibody in Eukaryotic Cells and Purification Thereof A method of co-transfecting FreeStyle 293F cells (purchased from Invitrogen, USA, catalog number: R790-07) can be used for the expression of the recombinant vector for the GB235-019 antibody constructed in Example 5. 24 hours prior to transfection, FreeStyle 293F cells were passaged at $6 \times 10^5$ cells/ml and cultured on a thermostatted shaker at the condition of 135 rpm, 37° C., 8% $CO_2$, so that the cell density (according to blood cell plate counting method) on the day of transfection was $1.2$-$1.5 \times 10^6$ cells/ml. The cells were diluted using FreeStyle 293 medium (purchased from Invitrogen Inc., USA, catalog number: 12338-018) to a density of $1 \times 10^6$ cells/ml. In order to ensure the best transfection, the cell viability (according to trypan blue staining method) should be greater than 95%.

The reagent for transfection FreeStyle Max Reagent (purchased from Invitrogen Inc., USA, catalog number: 16447-500) was gently reversed for 4 times for homogeneous mixing. 315 μg of each of the heavy chain and light chain expression vector plasmids was respectively added into the culture solution for transfection OptiPRO SFM (purchased from Invitrogen Inc., USA, catalog number: 12309-050). The volume was supplemented to 10 ml using OptiPRO SFM, and the mixture was mixed to homogeneity. In another centrifuge tube, 625 μl of FreeStyle Max Reagent was diluted to 10 ml using OptiPRO SFM. The tube was gently reversed for homogeneous mixing. The diluted plasmid and the diluted FreeStyle Max Reagent were mixed to homogeneity and incubated at room temperature for 15 minutes. The resulting 20 ml mixed solution was slowly added into a shake flask containing 500 ml of FreeStyle 293F medium (purchased from Invitrogen Inc., USA, catalog number: 12338-018). The shake flask was cultured on a thermostatted shaker for 7 days (135 rpm, 37° C., 8% $CO_2$). The culture was centrifuged in a refrigerated centrifuge at 9000 rpm for 20 minutes, and the supernatant was collected for subsequent protein purification.

The above-said FreeStyle 293F cell supernatant comprising the GB235-019 antibody was centrifuged. IgG1 isotype antibody was captured using Protein A column (purchased from GE Healthcare Bio-Sciences Inc., USA, catalog number: 17-5080-02), and eluted using 50 mM citric acid-sodium citrate buffer (pH 3.3). Eluant was collected (0.5 ml) and neutralized to neutral by addition of 100 μl of 1 M tris(hydroxymethyl)aminomethane-hydrochloric acid (Tris-HCl) buffer (pH 11.0). Then the eluant was dialyzed against a 10K dialysis membrane (purchased from Shanghai Generay Biotech Co, Ltd, catalog number: M1915) in phosphate buffer solution PBS (0.01 M $Na_2HPO_4 \cdot 12H_2O$+0.002 M $KH_2PO_4$+0.14 M NaCl+0.002 M KCl, pH=7.2), and the protein content was determined at OD280 nm. The resulting solution was filtered through a 0.22 μm filter (purchased from Millipore Inc., Germany, catalog number: GVHP01300) to be sterile, and the filtrate was stored at −80° C. The GB235-019 antibody obtained from purification was determined for its purity and molecular weight using 10% polyacrylamide gel electrophoresis under reducing condition of dithiothreitol at a final concentration of 50 mM.

Figure 2:
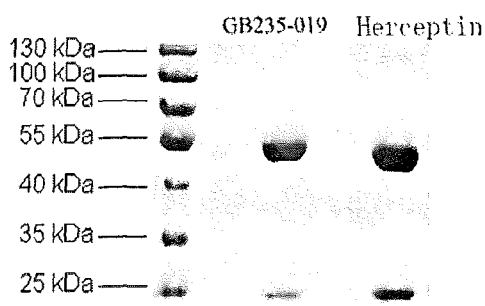
FIG. 2 shows the picture of the SDS-PAGE electrophoresis of the recombinant full-length anti-human HER2 antibody GB235-019. The purified GB235-019 and the Herceptin control sample were run on 10% polyacrylamide gel electrophoresis under reducing condition of 50 mM dithiothreitol. Results showed that both the GB235-019 antibody and the Herceptin antibody exhibited two bands having a molecular weight of 50 KDa and 25 KDa, which were respectively the heavy chain and the light chain of the antibodies.
Figure 2:

The results in FIG. 2 show that under completely reducing condition, the GB235-019 antibody exhibited two bands having a molecular weight of 50 KDa and 25 KDa respectively, which were the bands for the heavy chain and the light chain of the antibody (Herceptin served as the positive control, which was purchased from Roche Corp.). These results indicated that the GB235-019 antibody constructed had a correct structure and its molecular weight is consistent with the theoretical value.

Example 7

Analyzing the Reduced Molecular Weight of the GB235-019 Antibody

Into 10 μg of the GB235-019 antibody was added dithiothreitol at a final concentration of 20 mM, and the mixture was incubated in a water bath at 37° C. for 30 minutes to break all interchain disulfide bonds. The separated light chain and heavy chain were analyzed using reverse phase chromatography combined with mass spectrometry. A Waters H-Class Bio ultra high performance liquid chromatograph (Waters Inc., USA) was used, with chromatrography column: PLRP-S 300 Å, 3.0 μm, 2.1×150 mm (purchased from Agilent Inc., USA, catalog number: 1912-3301); mobile phase: A (water), B (acetonitrile) and C (1% trifluoroacetic acid), a gradient of 35% B at the $4^{th}$ minute was changed into 42% B at the $20^{th}$ minute, the C phase being maintained at 10%, the flow rate being 0.3 mL/min, and the loading amount being 20 μg. A Thermo LTQ-Orbitrap Discovery mass spectrometer (Thermo Fisher, USA) was used, with the spraying voltage being 3.7 KV, the tube lens being 230 V, the capillary temperature being 300° C., the resolution being 30000, and the range of mass-to-charge ratio being from 1000 to 3000. The theoretical molecular weight of the heavy chain (the Fc containing G0F glycan form) was calculated by GPMAW6.0 software to be 50416.7 Da, and the theoretical molecular weight of the light chain was 23120.8 Da. The original signals generated from mass spectrometry were deconvoluted using PROMASS software to obtain the corresponding measured molecular weight.

Figure 3A:
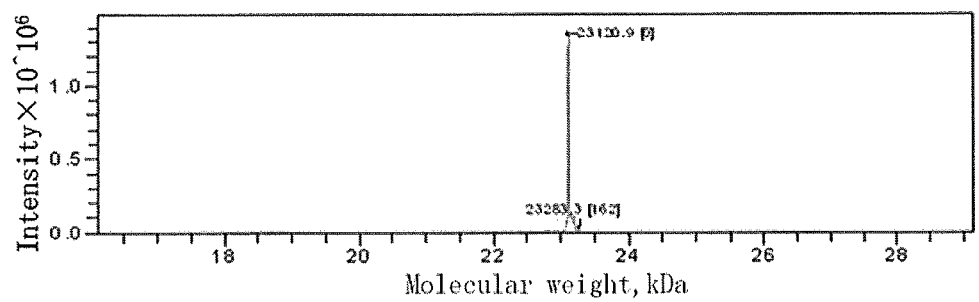
FIG. 3A and FIG. 3B show the results of analysis of reduced molecular weight of GB235-019. The GB235-019 antibody was analyzed on a Waters H-Class Bio ultra high performance liquid chromatograph under reducing condition of dithiothreitol, and the original signals from the mass spectrometry was deconvoluted using PROMASS software to obtain the corresponding measured molecular weight. The theoretical molecular weight of the heavy chain (the Fc containing G0F glycan form) was calculated by GPMAW6.0 software to be 50416.7 Da, and the theoretical molecular weight of the light chain was 23120.8 Da. The result in FIG. 3A shows that the measured molecular weight of the light chain of the GB235-019 antibody was consistent with the theoretical molecular weight, indicating absence of glycosylation in the light chain. The result in FIG. 3B shows that the measured molecular weight of the heavy chain of the GB235-019 antibody differed greatly from the theoretical molecular weight (>1500 Da). By aligning with the theoretical sequence, it was found that besides the Fc region, the Fab framework region also had the theoretical N-glycosylation site (Asn-Thr-Ser).
Figure 3B:
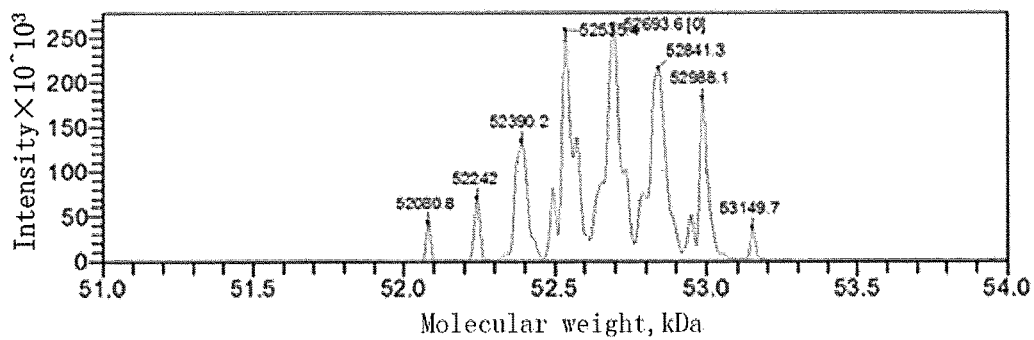

The result in FIG. 3A shows that the measured molecular weight of the light chain of the GB235-019 antibody was consistent with the theoretical molecular weight, indicating absence of glycosylation in the light chain. The result in FIG. 3B shows that the measured molecular weight of the heavy chain of the GB235-019 antibody differed greatly from the theoretical molecular weight (>1500 Da). By aligning with the theoretical sequence, it was found that besides the Fc region, the Fab framework region also had the theoretical N-glycosylation site (Asn-Thr-Ser), leading to the additional molecular weight.

Example 8

Construction of the Eukaryotic Expression Vector for GB235-019 with the Mutated Signature Sequence of N-Linked Glycan at the Fab End of the Heavy Chain The conservative N-glycosylation site was Asn-X-Thr/Ser, wherein X was any amino acid other than Pro. N-linked glycan was attached to the Asn residue in the Asn-X-Sen/Thr characteristic sequence (Imperiali B, O'Connor S E. Effect of N-linked glycosylation on glycopeptide and glycoprotein structure. Curr Opin Chem Biol 3 (6): 643-649). The Asn73 position in the Fab framework region 3 of the full-length antibody GB235-019 obtained in Example 5 was the N-glycosylation site. The conservative N-glycosylation site was removed by mutating the unique sequence of Asn-X-Ser/Thr (Walsh G. Biopharmaceutical benchmarks-2003. Nat Biotechnol, 2003, 21:865-870). IgBLAST alignment revealed the presence of the Asp-Thr-Ser combination in the Germline gene. As indicated by nucleotide sequence alignment, the codon "AAC" corresponding to Asn could be mutated to "GAC" to change Asn to Asp. Both Asn and Gln are amide-type amino acids, and they are conservative substitutions for each other in that Gln has one more methyl radical in the side chain group than Asn. Similarly, the codon "AAC" corresponding to Asn could be mutated to "CAG" in order to change Asn to Gln. IgBLAST revealed the presence of Ala in the position of Ser in the Germline gene. Germline nucleotide sequence alignment indicates that the codon "TCC" corresponding to Ser could be mutated to "GCC" to in order to replace Ser by Ala.

The heavy chain expression vectors for the mutated antibodies for GB235-019 Fab fragment with the mutated signature sequence of N-linked glycan were generated by point mutation using the full-length heavy chain eukaryotic expression vector obtained in Example 5 as template (Kunkel, T. A, et al. "Rapid and efficient site-specific mutagenesis without phenotypic selection. Proc. Natl. Acad. Sci, 1985 (82):488-492). Three mutation schemes were designed, which were mutation of Asn73 (N73) in the heavy chain of the GB235-019 antibody to Asp73 (D73), mutation of Asn73 (N73) in the heavy chain of the GB235-019 antibody to Gln73 (Q73), and mutation of Ser75 (S75) in the heavy chain of the GB235-019 antibody to Ala75 (A75) respectively. Primers were designed for constructing the heavy chain expression vector for the GB235-019 antibody with the above point mutations at the signature sequence of N-linked glycan at the Fab end of the GB235-019 antibody, the primers being as follows:

```
12-1:
5'-GTCACCATGACCAGGGACACCTCCAT-3'
(SEQ ID NO: 29)

12-2:
5'-ATGGAGGTGTCCCTGGTCATGGTGAC-3'
(SEQ ID NO: 30)

13-1:
5'-GTCACCATGACCAGGCAGACCTCCATAAGC-3'
(SEQ ID NO: 31)
```

-continued 13-2:
5'-GCTTATGGAGGTCTGCCTGGTCATGGTGAC-3'
(SEQ ID NO: 32)

14-1:
5'-CATGACCAGGAACACCGCCATAAGCAC-3'
(SEQ ID NO: 33)

14-2:
5'-GTGCTTATGGCGGTGTTCCTGGTCATG-3'
(SEQ ID NO: 34)

Using the 293-VH-CH expression vector obtained in Example 5 as template, and 12-1 and 12-2 as primers, a PCR product was obtained through amplification by PCR method. 2 µl of Dpn I (purchased from NEB Inc., USA, catalog number: 1235A) was added to 20 µl of the PCR product to perform digestion at 37° C. for 1 hour. The PCR product was purified using a PCR product purification kit (purchased from Axygen Inc., USA, catalog number: AP-PCR-50). The purified PCR product was transformed into DH5α *E. coli* competent cells (purchased from Tiangen Co., Ltd., catalog number: CB101) by heat shock method (42° C., 90 seconds). After identification through DNA sequencing, an eukaryotic expression vector of mutated antibody heavy chain was obtained, which was designated as "293-VH-CH-N73D" (which comprised the heavy chain variable region having the amino acid sequence and the nucleotide sequence of SEQ ID NO:10 and SEQ ID NO:13, respectively). Likewise, 13-1 and 13-2 were used as primers to obtain a PCR product through amplification by PCR method. 2 µl of DpnI (purchased from NEB Inc., USA, catalog number: 1235A) was added to 20 µl of the PCR product to perform digestion at 37° C. for 1 hour. The PCR product was purified using a PCR product purification kit (purchased from Axygen Inc., USA, catalog number: AP-PCR-50). The purified PCR product was transformed into DH5α *E. coli* competent cells (purchased from Tiangen Co., Ltd., catalog number: CBI01) by heat shock method (42° C., 90 seconds). After identification through DNA sequencing, an eukaryotic expression vector of mutated antibody heavy chain was obtained, which was designated as "293-VH-CH-N73Q" (which comprised the heavy chain variable region having the amino acid sequence and the nucleotide sequence of SEQ ID NO:11 and SEQ ID NO:14, respectively). And likewise, 14-1 and 14-2 were used as primers to obtain a PCR product through amplification by PCR method. 2 µl of DpnI (purchased from NEB Inc., USA, catalog number: 1235A) was added to 20 µl of the PCR product to perform digestion at 37° C. for 1 hour. The PCR product was purified using a PCR product purification kit (purchased from Axygen Inc., USA, catalog number: AP-PCR-50). The purified PCR product was transformed into DH5α *E. coli* competent cells (purchased from Tiangen Co., Ltd., catalog number: CB101) by heat shock method (42° C., 90 seconds). After identification through DNA sequencing, an eukaryotic expression vector of mutated antibody heavy chain was obtained, which was designated as "293-VH-CH-S75A" (which comprised the heavy chain variable region having the amino acid sequence and the nucleotide sequence of SEQ 11) NO:12 and SEQ ID NO:15. respectively).

Example 9

Transient Transfection Expression of the GB235-019 Mutated Antibodies in Eukaryotic Cells and Purification Thereof The expression of the recombinant vectors for mutated antibodies constructed in Example 8 was performed in the same procedure as in Example 6. 293-VH-CH-N73D, 293-VH-CH-N73Q and 293-VH-CH-S75A were respectively used with 293-VL-CL to co-transfect FreeStyle 293F cells (purchased from Invitrogen, USA, catalog number: R790-07).

The reagent for transfection FreeStyle Max Reagent (purchased from Invitrogen Inc., USA, catalog number: 16447-500) was gently reversed for 4 times for homogeneous mixing. 315 µg of each of the heavy chain and light chain expression vector plasmids was respectively added into the culture solution for transfection OptiPRO SFM (purchased from Invitrogen Inc., USA, catalog number: 12309-050). The volume was supplemented to 10 ml using OptiPRO SFM, and the mixture was mixed to homogeneity. In another centrifuge tube, 625 µl of FreeStyle Max Reagent was diluted to 10 ml using OptiPRO SFM. The tube was gently reversed for homogeneous mixing. The diluted plasmid and the diluted FreeStyle Max Reagent were mixed to homogeneity and incubated at room temperature for 15 minutes. The resulting 20 ml mixed solution was slowly added into a shake flask containing 500 ml of FreeStyle 293F medium (purchased from Invitrogen Inc., USA, catalog number: 12338-018). The shake flask was cultured on a thermostatted shaker for 7 days (135 rpm, 37° C., 8% $CO_2$). The culture was centrifuged in a refrigerated centrifuge at 9000 rpm for 20 minutes, and the supernatant was collected for subsequent protein purification. The method of purifying the mutated antibodies was the same as that in Example 6. The mutated antibodies obtained were filtered through a 0.22 µm filter (purchased from Millipore Inc., catalog number: (GVHP01300) to be sterile, and the filtrate was stored at −80° C. The mutated antibodies obtained from purification were respectively designated as GB235-019N73D, GB235-019N73Q and (GB235-019S75A. The mutated antibodies were determined for their purity and molecular weight using 10% polyacrylamide gel electrophoresis under reducing condition of dithiothreitol at a final concentration of 50 mM.

Figure 4:
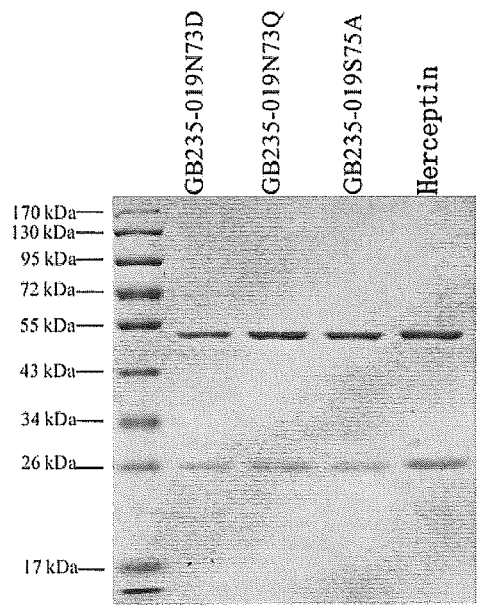
FIG. 4 shows the picture of SDS-PAGE electrophoresis of the GB235-019 mutated antibodies. The purified mutated antibodies GB235-019N73D, GB235-019N73Q and GB235-019S75A, and the Herceptin control sample were run on 10% polyacrylamide gel electrophoresis under reducing condition of 50 mM dithiothreitol. Results showed that the GB235-019 mutated antibodies and the Herceptin antibody all exhibited two bands having a molecular weight of 50 KDa and 25 Kda, which were respectively the heavy chain and the light chain of the antibodies.

The results in FIG. 4 show that under completely reducing condition, each of the GB235-019N73D, GB235-019N73Q and GB235-019S75A antibodies exhibited two bands having a molecular weight of 50 KDa and 25 KDa respectively, which were the bands for the heavy chain and the light chain of the respective antibodies (Herceptin served as the positive control, which was purchased from Roche Corp.). These results indicated that the GB235-019N73D, GB235-019N73Q and GB235-019S75A antibodies constructed had correct structures and molecular weights consistent with the theoretical value.

Example 10

Analysis of the Reduced Molecular Weights of the Recombinant Full-Length GB235-019 Mutated Antibodies The method of analyzing the reduced molecular weights of the mutated antibodies GB235-019N73D, GB235-019N73Q and (GB235-019575A obtained in Example 9 was the same as, that in Example 7. Into 10 µg of each of the GB235-019 mutated antibodies GB235-019N73D, GB235-019N73Q and GB235-019S75A was added dithiothreitol at a final concentration of 20 mM, and the mutated antibodies were incubated in a water bath at 37° C. for 30 minutes to break all interchain disulfide bonds. The separated light chain and heavy chain were analyzed using reverse phase chromatography combined with mass spectrometry. A Waters H-Class Bio ultra high performance liquid chromatograph (Waters Inc., USA) was used, with chromatography column: PLRP-S 300 Å, 3.0 µm, 2.1×150 mm (purchased from Agilent Inc., USA, catalog number: 1912-3301); mobile phase: A (water), B (acetonitrile) and C (1% TFA), a gradient of 35% B at the 4$^{th}$ minute to 42% B at the 20$^{th}$ minute, the C phase being maintained at 10%, the flow rate being 0.3 mL/min, and the loading amount being 20 µg. A Thermo LTQ-Orbitrap Discovery mass spectrometer (Thermo Fisher Inc., USA) was used, with the spraying voltage being 3.7 KV, the tube lens being 230 V, the capillary temperature being 300° C., the resolution being 30000, and the range of mass-to-charge ratio being from 1000 to 3000. The theoretical molecular weights of the heavy chains (the Fc containing G0F glycan form) of the three mutated antibodies was calculated by GPMAW6.0 software to be 50400.7 Da for GB235-019S75A, 50417.7 Da for GB235-019N73D and 50430.7 Da for GB235-019 N73Q. The original signals collected by the mass spectrometry was deconvoluted using PROMASS software to obtain the corresponding measured molecular weights.

Figure 5A:
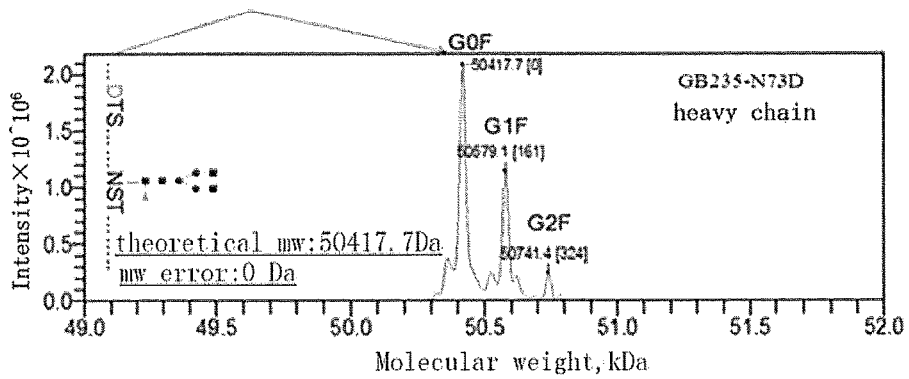
FIG. 5A, FIG. 5B and FIG. 5C show the results of analysis of reduced molecular weight of the GB235-019 mutated antibodies. The mutated antibodies GB235-019N73D, GB235-019N73Q and GB235-019S75A were analyzed on a Waters H-Class Bio ultra high performance liquid chromatograph under reducing condition of dithiothreitol, and the original signals detected by the mass spectrometry were deconvoluted using PROMASS software to obtain the corresponding measured molecular weight. The theoretical molecular weight of the heavy chain (the Fc containing G0F glycan form) was calculated by GPMAW6.0 software to be 50416.7 Da.
Figure 5B:
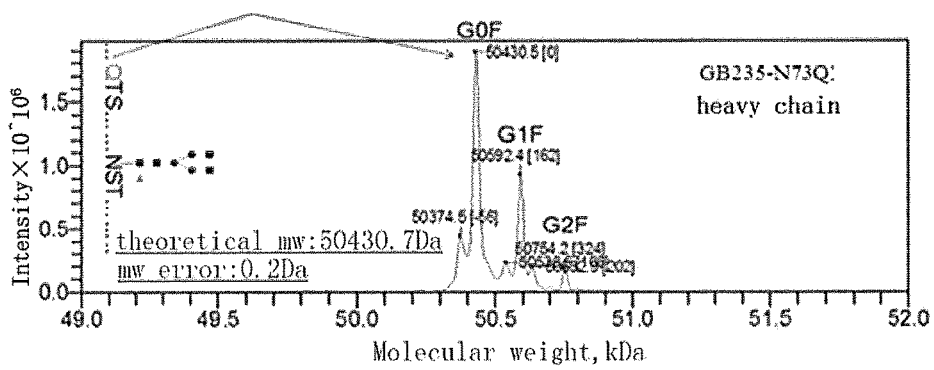
Figure 5C:
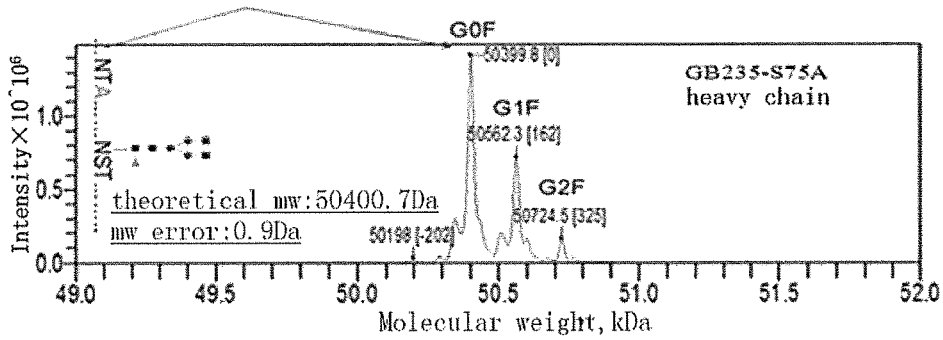

FIG. 5A shows that the measured molecular weight of the heavy chain of GB235-019N73D was consistent with the theoretical molecular weight, indicating absence of glycosylation in the heavy chain. FIG. 5B and FIG. 5C show that the measured molecular weight of the heavy chain of mutated antibodies GB235-019N73Q and GB235-019S75A was closely consistent with the theoretical molecular weight (with difference <1 Da), indicating that the N-glycosylation site in the Fab framework region had been removed.

There is a conservative N-linked glycosylation site Asn297 within the CH2 region in the Fc segment of the heavy chain of human IgG. The polysaccharide chain linked at Asn297 can maintain the quaternary structure of the antibody and the thermal stability of the Fc segment, and can regulate the antibody-dependent cellular cytotoxicity (ADCC), the complement-dependent cytotoxicity (CDC) and the half-life respectively by influencing the binding of the IgG molecule to FcRs, C1q and FcRn.

N-glycosylation modification of human IgG Fab may have an obvious promoting or inhibitory effect on the binding function of an antibody to an antigen. Minor changes in the position where glycosylation modification occurs may produce a totally different effect on the subsequent processing of polysaccharide chain and the binding activity of an antibody to an antigen, and cause complexity to quality control in antibody production process. The mutated antibodies GB235-019N73D, GB235-019N73Q and GB235-019S 75A were obtained after making point mutation in the GE235-019 wild-type antibody. The three mutated antibodies changed the specific site for N-linked glycan (Asn-Thr-Ser) of the heavy chain Fab in the GB235-019 wild-type antibody. Determination of reduced molecular weight of the three mutated antibodies revealed absence of glycosylation in the heavy chain Fab, which would be helpful for quality control in the production process. The three mutated antibodies were further validated by biological activity analysis and physico-chemical analysis.

Example 11

Identification of the Immunological Activity of the Recombinant Full-Length GB235-019 Wild-Type Antibody and Mutated Antibodies The binding capability of the GB235-019 wild-type antibody (GB235-019WT) and the mutated antibodies GB235-019N73D, GB235-019N73Q and GB235-019S75A to human HER2 antigen was validated using ELISA binding assay in a procedure as follows. Human HER2 antigen (purchased from Sino Biological Inc., catalog number: 10004-H08H) was diluted to 1 µg/ml using PBS buffer, and added to an ELISA plate at 100 µl/well to perform coating at 4° C. overnight. The plate was washed with PBST for four times, then 5% BSA (purchased front Amresco, USA, catalog number: 0332-100 g, the solution being PBS) was added at 300 µl/well to perform blocking at room temperature for 1 hour. After washing the plate with PBST for four times, each of the GB235-019WT antibody and the mutated antibodies GE235-019N73D, GB235-019N73Q and GB235-019S75A, and Pertuzumab (purchased from Roche Corp.) and Herceptin (purchased from Roche Corp.) respectively beginning with 5 µg/ml was subjected to 5-fold dilution to obtain 7 concentration gradients. Each of the dilutions was added to an ELISA plate at 100 µl/well and incubated at room temperature for 1 hour. The plate was washed with PBST for four times, then HRP-labeled goat anti-human IgG Fc antibody (purchased from CalBiochem Inc., USA, catalog number: AP113A-K) was diluted at 1:10000 with PBS buffer, and added to the ELISA plate at 100 µl/well to perform incubation at room temperature for 1 hour. The plate was washed with PBST for four times, then a solution of 3,3',5,5'-tetramethylbenzidine substrate (purchased from Tiangen Co., Ltd., catalog number: PA107-01) was added at 100 µl/well to perform incubation at room temperature for 15 minutes for visualization. A stop solution (1 M sulfuric acid) was added at 50 µl/well, and absorbance value was read at 450/630 nm wavelength on an M5 multi-functional ELISA plate (Molecular Devices Inc., USA).

Figure 6:
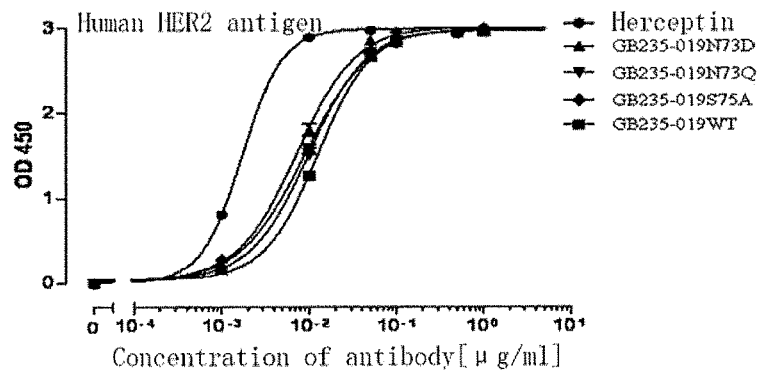
FIG. 6 shows the binding of the recombinant full-length anti-human HER2 GB235-019 mutated antibodies with human HER2 antigen. The ELISA plate was coated with human HER2 antigen, GB235-019WT, GB235-019N73D, GB235-019N73Q, GB235-019S75A antibodies and Herceptin and Pertuzumab at various concentrations were bound with the antigen molecules coated on the plate, and the bound antibodies were detected using HRP labeled goat anti-human IgG Fc antibody. The result in FIG. 6 shows that the GB235-019WT antibody as well as the mutated antibodies GB235-019N73D, GB235-019N73Q and GB235-019S75A had the capability to specifically bind to human HER2 antigen.

The results in FIG. 6 showed that the mutated antibodies GB235-019N73D, GB235-019N73Q and GB235-019S75A had the ability to specifically bind to human HER2 antigen, in a concentration-dependent and saturable manner. The mutated antibodies GB235-019N73D, GB235-019N73Q and GB235-019S75A had a similar binding ability to that of the GB235-019WT antibody, without significant difference.

Example 12

The Recombinant Full-Length GB235-019 Mutated Antibodies Inhibited In Vitro the Proliferation Activity of the Breast Cancer BT-474 Cells The breast cancer BT-474 cells express a moderate level of HER2 and HER3 and a high level of P-HER2, but do not express P-HER3 (Richard M. Neve. A collection of breast cancer cell lines for the study of functionally distinct cancer subtypes. CANCER CELL, 2006, 515-527). As defined hereinabove, the breast cancer BT-474 cells are HER2 positive tumor cells. In a proliferation inhibition assay using complete medium supplemented with Heregulin-α (purchased from R&D Inc., USA, catalog number: 296-HR), the BT-474 cells at log phase were cultured in a 96-well culture plate at 5000 cells/well in RPMI1640 complete medium (purchased from Invitrogen Inc., USA, catalog number: A10491) containing 10% fetal bovine serum (purchased from Invitrogen Inc., USA, catalog number: 10099-141) at 37° C. in 5% $CO_2$ for 24 hours. Inhibition assay was performed by administering the GB235-019WT antibody and the mutated antibodies GB235-019N73D, GB235-019N73Q and GB235-019S75A separately, as well as in combination with Herceptin. In the separate administration group, the GB235-019WT antibody and the GB235-019N73D, GB235-019N73Q and GB235-019S75A mutated antibodies and Pertuzumab and Herceptin were respectively added (at a final working concentration of 75, 18.8, 4.7, 1.2, 0.29, 0.07, 0.018, 0.005, 0.0011, and 0 μg/ml); and in the combined administration group, each of the above doses of GB235-019WT, GB235-019N73D, GB235-019N73Q, GB235-019S75A and Pertuzumab was administered in combination with Herceptin. After antibody treatment as above for 2 hours, Heregulin-α solution at a final working concentration of 100 ng/ml was added, with wells without addition of the Heregulin-α solution being included. The plate was further cultured at 37° C. in 5% $CO_2$ for 6 days. AlamarBlue (purchased from Invitrogen Inc., USA, catalog number: DAL1100) was added for detecting the viability of the BT-474 cells, and fluorescence value was read at 544/590 nm wavelength on an M5 multifunctional ELISA plate reader (Molecular Devices Inc., USA).

Figure 7A:
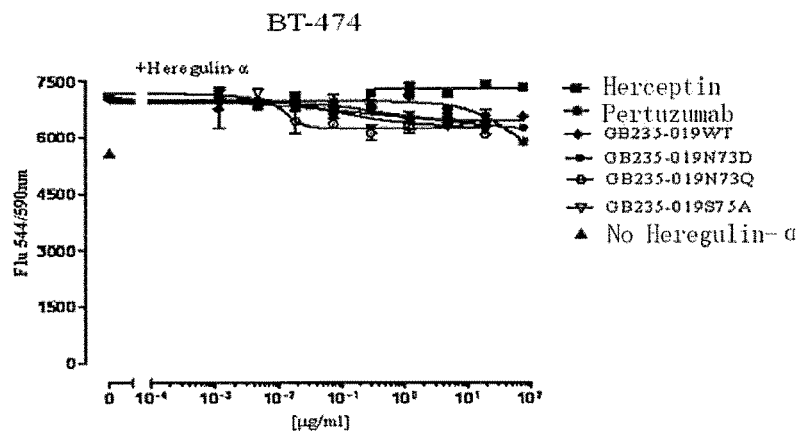
FIG. 7A shows the in vitro inhibitory effect of the recombinant full-length anti-human HER2 GB235-019 mutated antibodies on the proliferation of BT-474 cells. The HER2 positive BT-474 breast cancer cells expressing high level P-HER2 were incubated for 6 days in complete media supplemented with Heregulin-α. The cells were treated with GB235-019WT and separate administration of the mutated antibodies GB235-019WT antibody including GB235-019N73D, GB235-019N73Q and GB235-019S75A, as well as Herceptin, each alone at various concentrations. The cell viability was determined using Alarmar Blue. Results indicated that addition of Heregulin-α in the complete media induced proliferation of the BT-474 cells. The BT-474 cells became resistant to Herceptin administered separately, and the effect of the GB235-019WT antibody and the mutated antibodies GB235-019N73D, GB235-019N73Q and GB235-019S75A administered separately was not significant when used each alone.
Figure 7B:
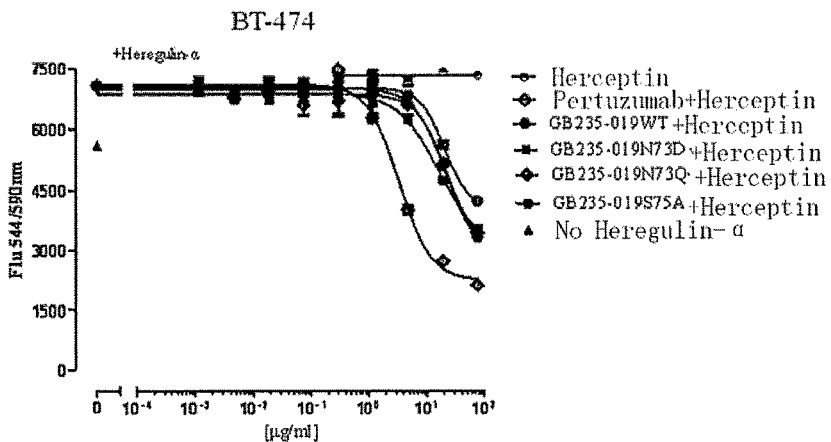
FIG. 7B shows the in vitro experiment results indicating that the Heregulin-α-induced resistance to Herceptin in the BT-474 cells was reversed by the recombinant full-length anti-human HER2 antibodies. The HER2 positive BT-474 breast cancer cells expressing high level P-HER2 were incubated for 6 days in complete media supplemented with Heregulin-α. The cells were then treated with combined administration of the GB235-019WT antibody and the mutated antibodies including GB235-019N73D, GB235-019N73Q and GB235-019S75A, each in combination with Herceptin. The cell viability was determined using Alarmar Blue. Results indicated that addition of Heregulin-α in the complete media induced proliferation of the BT-474 cells. The BT-474 cells became resistant to Herceptin administered separately, whereas combined administration of each of the GB235-019WT antibody and the mutated antibodies GB235-019N73D, GB235-019N73Q and GB235-019S75A in combination with Herceptin inhibited the. Heregulin-a-induced proliferation, markedly down to a level lower than that before Heregulin-a induction, in a concentration-dependent manner. The mutated antibodies GB235-019N73D, GB235-019N73Q and OB235-019S75A had an equivalent effect to that of the GB235-019WT antibody.

Results of the assay indicated that the recombinant full-length anti-HER2 mutated antibodies GB235-019N73D, GB235-019N73Q and GB235-019S75A reversed, in vitro, the resistance to Herceptin of the HER2 positive BT-474 cells induced by Heregulin-α. The result in FIG. 7A showed that addition of Heregulin-α in the complete medium induced proliferation of the BT-474 cells. The BT-474 cells became insensitive to Herceptin administered separately, and the mutated antibodies GB235-019N73D, GB235-019N73Q and GB235-019S75A had no inhibitory effect either when administered separately, similar to the effect of the GB235-019WT antibody. The result in FIG. 7B showed that the mutated antibodies GB235-019N73D, GB235-019N73Q and GB235-019S75A inhibited Heregulin-α-induced proliferation when each of them was administered in combination with Herceptin. Combined administration of each of the three mutated antibodies with Herceptin not only inhibited proliferation of the BT-474 cells induced by Heregulin-α, but also markedly inhibited to a level lower than that before Heregulin-α induction, in a concentration-dependent manner. The mutated antibodies GB235-019N73D, GB235-019N73Q and GB235-019S75A had a similar effect to that of the GB235-019WT antibody, without significant difference.

Example 13

In Vitro Inhibition of Breast Cancer BT-474 Cell Signal Transduction by the Recombinant Full-Length Anti-Human HER2 GB235-019 Mutated Antibodies The BT-474 cells at log phase were cultured in a 6-well culture plate at $1.8 \times 10^5$ cells/well in RPMI1640 complete medium (purchased from Invitrogen Inc., USA, catalog number: A10491) containing 10% fetal bovine serum (purchased from Invitrogen Inc., USA, catalog number: 10099-141) at 37° C. in 5% $CO_2$ for 24 hours. On the next day, the medium was discarded and low serum culture medium containing 0.1% fetal bovine serum (purchased from Invitrogen Inc., USA, catalog number: 10099-141) was used instead to incubate for 24 hours.

Then 20 μg /ml of each of the GB235-019WT and the GB235-019N73D mutated antibody, Herceptin and Pertuzumab was separately administered. After the BT-474 cells were treated with the antibodies for 6 hours, Heregulin-α (purchased from R&D Inc., USA, catalog number: 296-HR) was added at a final concentration of 100 ng/ml for induction for 15 minutes, with blank control wells without addition of Heregulin-α being included. The plate was washed with PBS pre-cooled at 4° C. once to stop reaction. Then 120 μl of LDS (purchased from Invitrogen Inc., USA, catalog number: NP0007) was added into the plate and put the plate stand on ice. Cell lysate was promptly collected and stored at −80° C. for later use.

The collected cell lysate was subjected to Western-blotting analysis under reducing condition of dithiothreitol (purchased from Sangon Inc., catalog number: D0281) at a final concentration of 50 mM to determine the effect of the antibodies on HER-3, Akt and ERk1/2 phosphorylation in the SK-BR-3 cells induced by Heregulin-α (purchased from R&D Inc., catalog number: 296-HR). Western-blotting was performed as follows. The proteins on the gel after electrophoresis were transferred by electrophoretic transfer method (300 mA, 80 minutes) onto an NC membrane (purchased from Pall Inc., USA, catalog number: S80209) and blocked with 5% dried skimmed milk (purchased from Sangon Inc., catalog number: NB0669). Then rabbit primary antibody P-HER3 Y1289 (purchased from Cell Signaling Technology Inc., USA, catalog number: 8017) diluted at 1:1000, rabbit primary antibody HER3 (purchased from Cell Signaling Technology Inc., USA, catalog number: 12708) diluted at 1:1000, rabbit primary antibody P-AktS473 (purchased from Cell Signaling Technology Inc., USA, catalog number: 4060) diluted at 1:1000, rabbit primary antibody Akt (purchased from Cell Signaling Technology Inc., USA, catalog number: 4691) diluted at 1:1000, rabbit primary antibody P-ERK1/2 (purchased from Cell Signaling Technology Inc., USA, catalog number: 4370) diluted at 1:500, rabbit primary antibody ERK1/2 (purchased from Cell Signaling Technology Inc., USA, catalog number: 4695) diluted at 1:1000 and rabbit primary antibody GAPDH (Cell Signaling Technology Inc., USA, catalog number: 5174) diluted at 1:5000 were added respectively to perform incubation at 4° C. overnight. The NC membrane was washed with 1×TBST for three times, then HRP-labeled goat anti-rabbit antibody (purchased from MERCK Inc., USA, catalog number: 401315) diluted at 1:10000 was added. The NC membrane was washed again with 1×TBST for three times, then ECL (purchased from PerkinElmer Inc., USA, catalog number: NEL104001EA) was added for visualization. A film (purchased from Kodak Inc., catalog number: FF057) was exposed to record the signals.

Figure 8:
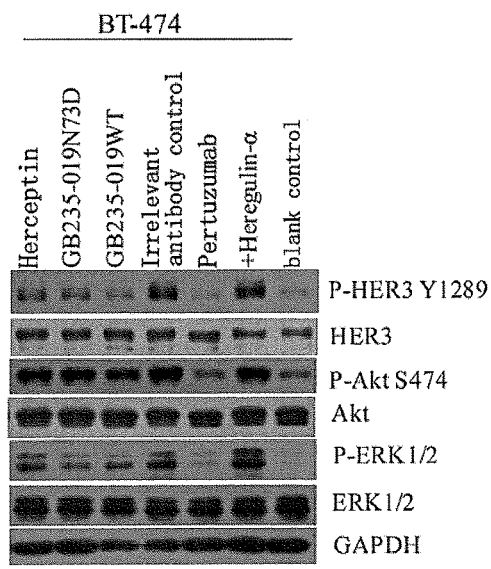
FIG. 8 shows the inhibitory effect of the recombinant full-length anti-human HER2 antibodies on signal transduction in breast cancer cell line BT-474. The HER2 positive BT-474 breast cancer cells highly expressing P-HER2 were subjected to starvation culture in 0.1% fetal, bovine serum medium for 24 hours. Then 20 µg/ml of each of the GB235-019WT antibody and the GB235-019N73D mutated antibody were added, and 20 µg/ml of Herceptin and 20 µg/ml of Pertuzumab were separately administered. After treating the BT-474 cells with the antibodies for 6 hours, Heregulin-α at a final concentration of 100 ng/ml was added to induce for 10 minutes, at which time samples were taken. Cell lysates were subjected to immunoblotting, and the whole and the phosphorylated HER3, Akt and ERK were detected respectively using corresponding antibodies. The results in FIG. 8 show that, compared with the control group without addition of Heregulin-α, Heregulin-α resulted in upregulation of HER3 phosphorylation in the BT-474 cells. Separately administered GB235-019WT and GB235-019N73D significantly inhibited Heregulin-α-induced upregulation of HER3 phosphorylation in the BT-474 cells, and completely reversed upregulation of HER3 phosphorylation induced by Heregulin-α. The efficacy of GB235-

Breast cancer BT-474 cells express a high level of P-HER2 but do not express P-HER3, and are a cell strain sensitive to Herceptin. The results in FIG. 8 show that Heregulin-α caused upregulation of HER3 phosphorylation in the BT-474 cells as compared with the control group without addition of Heregulin-α. The separately administered GB235-019 WT antibody and GB235-019N73D mutated antibody significantly inhibited upregulation of HER3 phosphorylation in the BT-474 cells induced by Heregulin-α, and completely reversed upregulation of HER3 phosphorylation induced by Heregulin-α, the GB235-019N73D mutated antibody having a similar effect to that of the GB235-019WT antibody. Pertuzumab also completely inhibited upregulation of HER3 phosphorylation in the BT-474 cells induced by Heregulin-α, and Herceptin also significantly inhibited upregulation of HER3 phosphorylation in the BT-474 cells induced by Heregulin-α.

The separately administered GB235-019WT antibody and GB235-019N73D mutated antibody did not inhibit upregulation of Akt phosphorylation induced by Heregulin-α. The separately administered Pertuzumab significantly inhibited upregulation of Akt phosphorylation induced by Heregulin-α. The separately administered GB235-019N73D mutated antibody and GB235-019WT antibody significantly inhibited upregulation of ERK1/2 phosphorylation induced by Hereguli-α, the GB235-019N73D mutated antibody having a similar effect to that of the GB235-019WT antibody.

Example 14

In Vitro Inhibition of Breast Cancer MCF7 Cell Signal Transduction by the Recombinant Full-Length Anti-Human HER2 GB235-019 Mutated Antibodies Breast cancer MCF 7 cells express a low level of HER2 and a high level of HER3, but do not express P-HER2 and P-HER3 (Richard M. Neve. A collection of breast cancer cell lines for the study of functionally distinct cancer subtypes. CANCER CELL, 2006: 515-527). As defined hereinabove, the breast cancer MCF 7 cells are HER2 negative tumor cells. The MCF 7 cells at log phase were cultured in a 6-well culture plate at $1.8 \times 10^5$ cells/well in RPMI1640 complete medium (purchased from Invitrogen Inc., USA, catalog number: A10491) containing 10% fetal bovine serum (purchased from Invitrogen Inc., USA, catalog number: 10099-141) for 24 hours. On the next day, the medium was discarded and low serum culture medium containing 0.1% fetal bovine serum was used instead to perform starvation culture for 24 hours. The MCF7 cells were treated with 20 μg/ml of each of the GB235-019WT antibody and the mutated antibodies GB235-019N73D, GB235-019N73Q and GB235-019S75A, and Pertuzumab and Herceptin administered separately or in combination in RPMI-0.1% fetal bovine serum culture solution for 6 hours. Then Hereguli-α (purchased from R&D Inc., USA, catalog number: 296-HR) was added at a working final concentration of 100 ng/ml for induction for 10 minutes, with blank control wells without addition of Hereguli-α being included. The plate was washed with PBS pre-cooled at 4° C. once to stop reaction. Then 120 μl of LDS (purchased from Invitrogen Inc., USA, catalog number: NP0007) was added into the plate and put the plate on ice. Cell lysate was promptly collected and stored at −80° C. for later use.

The collected cell lysate was subjected to Western-blotting analysis under reducing condition of dithiothreitol at a final concentration of 50 mM to determine the effect of the antibodies on HER-3 phosphorylation in the MCF 7 cells induced by Hereguli-α, as well as the effect of the antibodies on Akt and ERK1/2 phosphorylation downstream of HER3. Western-blotting analysis was performed in the same procedure as in Example 13.

FIG. 9 shows inhibition of HER2 negative breast cancer MCF 7 cell signal transduction by the GB235-019 mutated antibodies. Results indicated that Hereguli-α induced upregulation of HER3 phosphorylation in the MCF 7 cells as compared to the control group without addition of Hereguli-α. Each of the separately administered GB235-019WT antibody and the mutated antibodies GB235-019N73D, GB235-019N73Q and GB235-019S75A markedly inhibited upregulation of HER3 phosphorylation in the MCF 7 cells induced by Hereguli-α; GB235-019N73D completely reversed upregulation of HER3 phosphorylation induced by Hereguli-α; the separately administered Herceptin also markedly inhibited upregulation of HER3 phosphorylation in the MCF 7 cells induced by Hereguli-α; and Pertuzumab completely reversed upregulation of HER3 phosphorylation induced by Hereguli-α. Each of the separately administered GB235-019WT antibody and the mutated antibodies GB235-019N73D, GB235-019N73Q and GB235-019S75A markedly inhibited upregulation of Akt phosphorylation in the MCF 7 cells induced by Hereguli-α; and Pertuzumab completely reversed upregulation of Akt phosphorylation induced by Hereguli-α. Each of the separately administered GB235-019WT antibody and the mutated antibodies GB235-019N73D, GB235-019N73Q and GB235-019S75A markedly inhibited upregulation of ERK1/2 phosphorylation in the MCF 7 cells induced by Hereguli-α; and Pertuzumab completely reversed upregulation of ERK1/2 phosphorylation induced by Hereguli-α. Therefore, the antibodies of the present invention can also be used to treat HER2 negative tumors.

Example 15

Molecular Size Exclusion Chromatographic Analysis of the GB235-019 Mutated Antibodies The GB235-019 mutated antibodies GB235-019N73D, GB235-019N73Q and GB235-019S75A were respectively subjected to molecular size exclusion chromatography (SEC-HPLC) to determine their purity. The experiment conditions were as follows: Waters 2695 liquid chromatograph (Waters Inc., USA); TSKgel G3000SWXL chromatography columns in series (2 columns) (purchased from, Waters Inc., USA); the mobile phase being 0.1 M phosphate buffer, 0.1 M sodium chloride, pH 7.0, 1.0 mL/min, isocratic hold for 30 minutes; the loading amount being 30 μg of each of the antibodies; and the detection wavelength being 280 nm.

FIG. 10 shows the molecular size exclusion chromatogram of the three mutated antibodies. Small amounts of polymers and fragment molecules are present in the three antibodies, although the contents were low. Table 4 summarized the results of purity of the corresponding antibodies according to molecular size exclusion chromatography. The purity of the main peak of the GB235-019N73D antibody was 88.3%, the purity of the main peak of the GB235-019N73Q antibody was 89.7%, and the purity of the main peak of the GB235-019S75A antibody was 93.1%, the purity of the main peak of all of the three mutated antibodies being higher than 85%.

TABLE 4

Results of purity of the GB235-019 mutated antibodies according to molecular size exclusion chromatography

| Mutated antibody | % high-molecular-weight impurities (HMW) | % main peak (Main) | % low-molecular-weight impurities (LMW) |
|---|---|---|---|
| GB235-019S75A | 2.7 | 93.1 | 4.2 |
| GB235-019N73Q | 3.9 | 89.7 | 6.4 |
| GB235-019N73D | 8.2 | 88.3 | 3.5 |

Example 16

Imaging Capillary Isoelectric Focusing Analysis of the GB235-019 Mutated Antibodies The mutated antibodies GB235-019N73D, GB235-019N73Q and GB235-019S75A were respectively subjected to imaging capillary isoelectric focusing (iCIEF) to determine the isoelectric point (pI) of the respective main peaks and the purity of the charge isomers. The experiment conditions were as follows: ProteinSimple iCE280 capillary isoelectric focusing apparatus (Protein Simple Inc., USA); iCIEF cartridge (purchased from Protein Simple Inc., USA); amphoteric electrolyte solution was prepared by mixing 12

µl of Pharmalyte 3-10 (purchased from GE Inc., USA, catalog number: 17045601), 0.5 µl of pI Marker 5.85 (purchased from GE Inc., USA, catalog number: 17-0472-01), 0.5 µl of pI Marker 9.77 (purchased from GE Inc., USA, catalog number: 17-0473-01), 2 µl of 500 mM L-arginine (purchased from Sangon Inc., catalog number: AB0205-100g), 2 µl of 200 mM iminodiacetic acid (purchased from Sangon Inc., catalog number: IB0530-100g), 70 µl of 1% methylcellulose (purchased from Sangon Inc., catalog number: MB0616-250g) and 113 µl of 5.3 M urea (purchased from Sangon Inc., catalog number: UB0148-500g). The loading solution was prepared by mixing 180 µl of the amphoteric electrolyte solution with 20 µl of 2.5 mg/mL protein solution. The sample system was pre-focused at 1,500 V for 1 minute, and focused at 3,000 V for 10 minutes. Focusing patterns were captured using a CCD camera, with the detection wavelength of 280 nm.

FIG. 11 shows the electrophoregrams of imaging capillary isoelectric focusing electrophoresis of the three mutated antibodies. Table 5 summarizes the results of the isoelectric point of the corresponding main peaks and the purity of the charge isomers of the three mutated antibodies. The three mutated antibodies had a measured isoelectric point in the range of around 9.4 to 9.6. The isoelectric point of GB235-019N73D was about 0.1 lower than that of GB235-019N73Q and GB235-019S75A, and its, main peak purity was relatively the highest.

TABLE 5

Results of the isoelectric point of the main peaks and the purity of the charge isomers of GB235-019 mutated antibodies

| Mutated antibody | pI | % acidic peak (Acidic) | % main peak (Main) | % basic peak (Basic) |
|---|---|---|---|---|
| GB235-019S75A | 9.54 | 10.5 | 74.5 | 15.0 |
| GB235-019N73Q | 9.55 | 10.2 | 73.3 | 16.5 |
| GB235-019N73D | 9.42 | 11.9 | 77.2 | 10.9 |

Example 17

Capillary Gel Electrophoresis Analysis of the GB235-019 Mutated Antibodies

The mutated antibodies GB235-019N73D, GB235-019N73Q and GB235-019S75A were respectively subjected to reducing capillary gel electrophoresis analysis (rCE-SDS) to determine their respective purity (the sum of the percentage of the light chain and the heavy chain). The experiment conditions were as follows, SDS-MW Analysis Kit (purchased from Beckman Inc., USA, catalog number: 390953) and uncoated capillary tube (purchased from Micro solv Inc.) were used for analysis. 100 mM Tris-FIC1, pH 9.0, 1% SDS (purchased from Sangon Inc., catalog number: SB0485-100g) solution was mixed with β-mercaptoethanol (purchased from Sigma Inc., USA, catalog number: M6250) in a proportion of 55:5, 60 µl of the above mixed solution was mixed with 40 µl of 2.5 mg/mL sample solution and incubated in a water bath at 70° C. for 10 minutes. Sample loading was performed at 5 KV for 20 seconds, and separation was performed at 15 KV for 30 minutes. A UV detector was used, the wavelength being set at 214 nm.

FIG. 12 shows the electrophoregrams of reducing capillary gel electrophoresis of the three mutated antibodies. Table 6 summarizes the results of purity in terms of the sum of the light chain and the heavy chain of the three mutated antibodies. The three mutated antibodies all had small amounts of low molecular weight impurities and high molecular weight impurities. GB235-019N73D had relatively the least impurity content, and its purity in terms of the sum of the light chain and the heavy chain (LC+HC) was the highest.

TABLE 6

Results of purity of the GB235-019 mutated antibodies according to reducing capillary gel electrophoresis

| Mutated antibody | % light chain (LC) | % low-molecular-weight impurities (LMW) | % non-glycosylated chain (NGHC) | % heavy chain (HC) | % high-molecular-weight impurities (HMW) | % sum of light chain and heavy chain (LC + HC) |
|---|---|---|---|---|---|---|
| GB235-019S75A | 31.1 | 0.6 | 0.7 | 67.0 | 0.6 | 98.1 |
| GB235-019N73Q | 30.9 | 1.7 | 1.0 | 65.7 | 0.7 | 96.6 |
| GB235-019N73D | 31.2 | 0.1 | 0.5 | 67.6 | 0.6 | 98.8 |

Example 18

Differential Scanning Calorimetric Analysis of the GB235-019 mutated antibodies

The mutated antibodies GB235-019N73D, GB235-019N73Q and GB235-019S75A were respectively subjected to differential scanning calorimetry (DSC) to determine the respective Tm value (phase transit temperature, meaning that 50% of the biological molecules were in an unfolded state at that temperature). The experiment conditions were as follows. A MicroCal VP-Capillary DSC differential scanning calorimeter (GE Inc., USA) having a detection cell volume of 130 µl was used. The three mutated antibodies were respectively diluted with PBS (0.01 M $Na_2HPO_4 \cdot 12H_2O$+0.002 M $KH_2PO_4$+0.14 M NaCl +0.002 M KCl, pH=8.6) to 0.9 mg/mL. PBS was used as blank control, the temperature change was set at from 30° C. to 95° C., and the scanning speeding was 60° C./h.

FIG. 13 shows the differential scanning calorimetry diagrams of the three GB235-019 mutated antibodies. The Tm1 of said three molecules varied. The Tm1 of GB235-019N73Q was relatively the lowest, while that of GB235-019N73Q was close to that of GB235-019S75A. The higher the Tm value, the better the thermal stability. The difference in Tm1 indicates to some extent that the mutation has some effect on the CH2 domain. GB235-019N73D and GB235-019S75A had a better thermal stability than GB235-019N73Q.

We previously obtained a fully human anti-human HER2 (Her-2/neu) monoclonal antibody GB235-019 by using fully human scFV phage library screening technology and genetic engineering recombination expression technology (reference can be made to the Chinese Patent Application No. 201410705404.0). GB235-019 could bind to human HER2, monkey HER2 and mouse HER2 in a concentration-dependent and saturable manner, but it could not bind to human HER1, HER3 and HER4 antigens. Administration of GB235-019 in combination with Herceptin could reverse resistance to Herceptin of the BT-474 cells induced by the HER3 ligand Heregulin-α, and separate administration of GB235-019 inhibited upregulation of HER3 phosphorylation in the BT-474 cells induced by the HER3 ligand Heregulin-α. Also, administration of GB235-019 in combination with Herceptin could reverse resistance to Herceptin of the SK-BR-3 cells caused by the HER ligand Heregulin-α, which is similar to Pertuzumab. Administration of GB235-019 in combination with Herceptin could significantly inhibit the growth of human breast cancer (KPL-4) xenograft in mice. The Asn73 in the Fab framework region 3 of GB235-019 was the N-glycosylation site, and it was found through determination of reduced molecular weight that there was a complex polysaccharide chain present on GB235-019 Fab. N-glycosylation modification of human IgG Fab may have an obvious promoting or inhibitory effect on the binding function of an antibody to an antigen. Minor changes in the position where glycosylation modification occurs may produce a totally different effect on the subsequent processing of polysaccharide chain and the binding activity of an antibody to an antigen, and cause complexity to quality control in antibody production process. Three mutated antibodies GB235-019N73D, GB235-019N73Q and GB235-019S75A were obtained after making point mutation in the GB235-019 wild-type antibody. The three mutated antibodies changed the signature sequence for N-linked glycan (Asn-Thr-Ser) of the heavy chain Fab in the GB235-019 wild-type antibody. Through determination of reduced molecular weight, it was confirmed that the three mutated antibodies were not glycosylated in the heavy chain Fab.

Identification of immunological activity revealed that the mutated antibodies GB235-019N73D, GB235-019N73Q and GB235-019S75A had the capability to specifically bind to human HER2 antigen in a concentration-dependent and saturable manner. The mutated antibodies GB235-019N73D, GB235-019N73Q and GB235-019S75A had a similar binding capability to that of the GB235-019WT antibody, without significant difference, Administration of each of the mutated antibodies GB235-019N73D, GB235-019N73Q and GB235-019S75A in combination with Herceptin inhibited proliferation induced by Heregulin-α. Administration of each of the three mutated antibodies in combination with Herceptin not only inhibited proliferation of the BT-474 cells induced by Heregulin-α, but also markedly inhibited down to a level lower than that before Heregulin-α induction, in a concentration-dependent manner. The three mutated antibodies also had an effect similar to that of GB235-019WT antibody, without significant difference. Separate administration of the GB235-019N73D mutated antibody significantly inhibited upregulation of HER3 phosphorylation in the BT-474 cells induced by Heregulin-α, the effect of the GB235-019N73D mutated antibody being similar to that of the GB235-019WT antibody. Separate administration of each of the GB235-019N73D mutated antibody and the GB235-019WT antibody significantly inhibited upregulation of ERK1/2 phosphorylation in the BT-474 cells induced by Heregulin-α, the effect of the Gb235-019N73D mutated antibody being similar to that of the GB235-019WT antibody. Separate administration of each of the GB235-019WT antibody and the mutated antibodies GB235-019N73D, Gb235-019N73Q and GB235-019S75A markedly inhibited upregulation of HER3 phosphorylation in the MCF7 cells induced by Heregulin-α, and GB235-019N73D completely reversed upregulation of HER3 phosphorylation in the MCF7 cells induced by Heregulin-α. Separate administration of each of the Gb235-019WT antibody and the mutated antibodies GB235-019N73D, GB235-019N73Q, and GB235-019S75A markedly inhibited upregulation of Akt phosphorylation in the MCF7 cells induced by Heregulin-α. Separate administration of each of the GB235-019WT antibody and the mutated antibodies GB235-019N73D, GB235-019N73Q and GB235-019S75A markedly inhibited upregulation of ERK1/2 phosphorylation in the MCF7 cells induced by Heregulin-α, which further confirmed the biological activity of the three mutated antibodies. In summary of the above, the antibodies of the present invention can be used to not only treat HER2 positive tumors, but also treat HER2 negative tumors.

We analyzed the physical and chemical properties of the mutated antibodies GB235-019N73D, GB235-019N73Q and GB235-019S75A. Analysis of the three mutated antibodies by molecular size exclusion chromatography revealed that the purity of the main peak of the GB235-019N73D antibody was 88.3%, the purity of the main peak of the GB235-019N73Q antibody was 89.7%, and the purity of the main peak of the GB235-019S75A antibody was 93.1%, in which the purity of the main peak of all of the three mutated antibodies was higher than 85%. Imaging capillary isoelectric focusing (iCIEF) revealed the isoelectric point (pI) of the respective main peaks and the purity of the charge isomers of the three mutated antibodies. The three mutated antibodies had a measured isoelectric point in the range of around 9.4 to 9.6. The isoelectric point of GB235-019N73D was about 0.1 lower than that of GB235-019N73Q and GB235-019S75A, and its main peak purity was relatively the highest. Reducing capillary gel electrophoresis analysis (rCE-SDS) revealed the respective purity (the sum of the percentage of the light chain and the heavy chain) of the three mutated antibodies. The three mutated antibodies all had small amounts of low molecular weight impurities and high molecular weight impurities. GB235-019N73D had relatively the least impurity content, and its purity in terms of the sum of the light chain and the heavy chain (LC+HC) was the highest. Differential scanning calorimetry (DSC) revealed the respective Tm value (phase transit temperature, meaning that 50% of the biological molecules were in an unfolded state at that temperature) of the three mutated antibodies. The Tm1 of the three molecules varied. The Tm1 of GB235-019N73Q was relatively the lowest, while that of GB235-019N73Q was close to that of GB235-019S75A. The higher the Tm value, the better the thermal stability. The difference in Tm1 indicates to some extent that the mutation has some effect on the CH2 domain. GB235-019N73D and GB235-019S75A had a better thermal stability than GB235-019N73Q.

The invention claimed is:

1. A mutated fully human anti-HER2 antibody, comprising the amino acid sequence of SEQ ID NO:10 and SEQ ID NO:2; SEQ ID NO:11 and SEQ ID NO:2; or SEQ ID NO:12 and SEQ ID NO:2 for the heavy chain variable region and the light chain variable region of the antibody, respectively.

2. The mutated fully human anti-HER2 antibody according to claim 1, which is in the form of Fab, Fab', F(ab')$_2$, or scFv.

3. The mutated fully human anti-HER2 antibody according to claim 1, further comprising the heavy chain constant region and the light chain constant region of human IgG.

4. The mutated fully human anti-HER2 antibody according to claim 3, wherein the human IgG is IgG1.

5. The mutated fully human anti-HER2 antibody according to claim 3, wherein the amino acid sequence of the human IgG heavy chain constant region is SEQ ID NO:5, and the amino acid sequence of the human IgG light chain constant region is SEQ ID NO:6.

6. A pharmaceutical composition comprising the mutated fully human anti-HER2 antibody according to claim 1 and a pharmaceutically acceptable carrier.

7. A combined medicament comprising the mutated fully human anti-HER2 antibody of claim 1 and additional HER2 positive tumor therapeutic agent(s).

8. The combined medicament according to claim 7, wherein said additional HER2 positive tumor therapeutic agent(s) is herceptin or pertuzumab.

9. A kit for detecting human HER2 comprising the mutated fully human anti-HER2 antibody according to claim 1.

10. A method for treating a HER2 positive tumor in a subject, comprising administering to the subject the mutated fully human anti-HER2 antibody of claim 1.

11. The method according to claim 10, wherein the subject is a human having a HER2 positive tumor.

12. The method according to claim 10, wherein said HER2 positive tumor is selected from HER2 positive breast cancer, gastric cancer, lung cancer, non-small cell lung cancer, bone cancer, pancreatic cancer, skin cancer, head or neck cancer, cutaneous or intraocular melanoma, uterine cancer, ovary cancer, rectal cancer, anal cancer, colon cancer, fallopian tube cancer, endometrial cancer, cervical cancer, vaginal cancer, vulvar cancer, Hodgkin's disease, esophageal cancer, small intestine cancer, endocrine system cancer, thyroid cancer, parathyroid cancer, adrenal gland cancer, soft tissue cancer, urethra cancer, penis cancer, prostate cancer, bladder cancer, kidney cancer, kidney cell cancer, renal pelvis cancer, mesothelioma, liver cell cancer, gallbladder cancer, chronic or acute leukemia, lymphatic cell lymphoma, central nerve system cancer, spinal tumor, neuroglioma of brain stem, glioblastoma multiforme, astrocytoma, neurilemmoma, ependymoma, medulloblastoma, meningioma, squamous cell carcinoma and pituitary adenoma.

* * * * *

UNITED STATES PATENT AND TRADEMARK OFFICE
CERTIFICATE OF CORRECTION

PATENT NO. : 10,253,108 B2
APPLICATION NO. : 15/304199
DATED : April 9, 2019
INVENTOR(S) : Zhou et al.

Page 1 of 1

It is certified that error appears in the above-identified patent and that said Letters Patent is hereby corrected as shown below:

On the Title Page

Item (54) Title: Please correct "HUMANIZED" to read -- HUMAN --

Item (30) Foreign Application Priority Data: Please correct "2015 1 0051280" to read -- 2015 1 0051280.3 --

In the Specification

Column 1, Line 2: Please correct "HUMANIZED" to read -- HUMAN --

Column 6, Line 39: Please correct "Heregulin-a" to read -- Heregulin-α --

Column 6, Line 41: Please correct "Heregulin-a" to read -- Heregulin-α --

Column 9, Line 40: Please correct "100 μm/ml" to read -- 100 μg/ml --

Column 11, Line 23: Please correct "HER4-Fe" to read -- HER4-Fc --

Column 18, Line 58: Please correct "(GB235-019575A" to read -- GB235-019575A --

Column 22, Line 8: Please correct "ERk1/2" to read -- ERK1/2 --

Column 25, Line 41: Please correct "its, main" to read -- its main --

Column 27, Line 48: Please correct "difference, Administration" to read -- difference. Administration --

Signed and Sealed this
Sixteenth Day of July, 2019

Andrei Iancu
*Director of the United States Patent and Trademark Office*